(12) United States Patent
Bae et al.

(10) Patent No.: US 12,306,191 B2
(45) Date of Patent: May 20, 2025

(54) COMPOSITION FOR DIAGNOSIS OF DEGENERATIVE NEUROLOGICAL DISEASES

(71) Applicant: KYUNGPOOK NATIONAL UNIVERSITY INDUSTRY—ACADEMIC COOPERATION FOUNDATION, Daegu (KR)

(72) Inventors: Jae-Sung Bae, Daegu (KR); Hee Kyung Jin, Daegu (KR); Ju Youn Lee, Daegu (KR); Seung Hoon Han, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 1280 days.

(21) Appl. No.: 16/982,500

(22) PCT Filed: Mar. 21, 2019

(86) PCT No.: PCT/KR2019/003284
§ 371 (c)(1),
(2) Date: Sep. 18, 2020

(87) PCT Pub. No.: WO2019/182371
PCT Pub. Date: Sep. 26, 2019

(65) Prior Publication Data
US 2021/0003595 A1 Jan. 7, 2021

(30) Foreign Application Priority Data

Mar. 21, 2018 (KR) .................. 10-2018-0032669
Oct. 24, 2018 (KR) .................. 10-2018-0127656

(51) Int. Cl.
*G01N 33/68* (2006.01)
*A61K 31/164* (2006.01)
(Continued)

(52) U.S. Cl.
CPC ....... *G01N 33/6896* (2013.01); *A61K 31/164* (2013.01); *G01N 33/5008* (2013.01);
(Continued)

(58) Field of Classification Search
None
See application file for complete search history.

(56) References Cited

U.S. PATENT DOCUMENTS

2002/0051777 A1 5/2002 Gamble et al.
2005/0002859 A1 1/2005 Marnett et al.
(Continued)

FOREIGN PATENT DOCUMENTS

JP H08113535 A 5/1996
WO WO 00/52173 A2 9/2000
(Continued)

OTHER PUBLICATIONS

Yermakova et al., Downregulation of neuronal cyclooxygenase-2 expression in end stage Alzheimer's disease, Neurobiology of Aging 22, pp. 823-836, 2001. (Year: 2001).*
(Continued)

*Primary Examiner* — Rebecca M Giere
(74) *Attorney, Agent, or Firm* — James S. Keddie; Bozicevic, Field & Francis LLP

(57) ABSTRACT

The present invention relates to a composition for diagnosis of degenerative neurological diseases and, more specifically, to a composition for diagnosis of degenerative neurological diseases, comprising an agent for measuring the level of acetylation of COX2.
According to the present invention, since acetylation of COX2 in degenerative neurological diseases is significantly
(Continued)

reduced, whether COX2 is acetylated may be utilized as a diagnostic marker for degenerative neurological diseases, and it is possible to diagnose degenerative neurological diseases more rapidly and accurately by using same.

3 Claims, 33 Drawing Sheets

Specification includes a Sequence Listing.

(51) Int. Cl.
    *G01N 33/50*     (2006.01)
    *G01N 33/573*     (2006.01)

(52) U.S. Cl.
    CPC . *G01N 33/573* (2013.01); *G01N 2333/90241* (2013.01); *G01N 2440/10* (2013.01)

(56) References Cited

U.S. PATENT DOCUMENTS

| | | |
|---|---|---|
| 2010/0216882 A1 | 8/2010 | Serhan et al. |
| 2013/0251731 A1 | 9/2013 | Lee et al. |

FOREIGN PATENT DOCUMENTS

| | | |
|---|---|---|
| WO | WO 01/85953 A1 | 11/2001 |
| WO | WO 2004/061107 A1 | 7/2004 |
| WO | WO 2008/094713 A2 | 8/2008 |
| WO | WO 2017/103892 A2 | 6/2017 |

OTHER PUBLICATIONS

Hoozemans et al., Cyclooxygenase-1 and -2 in the Different Stages of Alzheimer's Disease Pathology, Current Pharmaceutical Design, 2008, 14, pp. 1419-1427. (Year: 2008).*

Lucido et al., "Crystal Structure of Aspirin-Acetylated Human Cyclooxygenase-2: Insight into the Formation of Products with Reversed Stereochemistry", Biochemistry, 2016, 55: 1226-1238.

Kalgutkar et al., "Aspirin-like Molecules that Covalently Inactivate Cyclooxygenase-2", Science, May 22, 1998, 280: 1268-1270.

Jung et al., "Short-chain C2 ceramide induces heme oxygenase-1 expression by upregulating AMPK and MAPK signaling pathways in rat primary astrocytes", Neurochemistry International, 2016, 94: 39-47.

Goodman et al., "Ceramide Protects Hippocampal Neurons Against Excitotoxic and Oxidative Insults, and Amyloid β-Peptide Toxicity", Journal of Neurochemistry, 1996, 66: 869-872.

Furuya et al., "Cell Permeable Exogenous Ceramide Reduces Infarct Size in Spontaneously Hypertensive Rats Supporting In Vitro Studies That Have Implicated Ceramide in Induction of Tolerance to Ischemia", Journal of Cerebral Blood Flow and Metabolism, 2001, 21(3): 226-232.

Jung et al., "Anti-inflammatory mechanism of exogenous C2 ceramide in lipopolysaccharide-stimulated microglia", Biochimica et Biophysica Acta, 2013, 1831: 1016-1026.

Chen et al., "The Protective Effect of Ceramide in Immature Rat Brain Hypoxia-Ischemia Involves Up-regulation of Bcl-2 and Reduction of TUNEL-Positive Cells", Journal of Cerebral Blood Flow and Metabolism, 2001, 21(1): 34-40.

Medeiros et al., "Aspirin-Triggered Lipoxin A4 Stimulates Alternative Activation of Microglia and Reduces Alzheimer Diseasee-Like Pathology in Mice", The American Journal of Pathology, May 2013, 182(5): 1780-1789.

Zhang et al., "Effects of Small Interfering RNA Targeting Sphingosine Kinase-1 Gene on the Animal Model of Alzheimer's Disease", J Huazhong Univ Sci Technol [Med Sci], 2013, 33(3): 427-432.

Lee et al., "Neuronal SphK1 acetylates COX2 and contributes to pathogenesis in a model of Alzheimer's Disease", Nature Communications, 2018, 9:1479, DOI: 10.1038/s41467-018-03674-2.

Aid et al., "Targeting cyclooxygenases-1 and -2 in neuroinflammation: Therapeutic implications", Biochimie, 2011, 93: 46-51.

Serhan et al., "Anti-Inflammatory and Pro-Resolving Lipid Mediators", Annu Rev Pathol., 2008, 3: 279-312.

* cited by examiner

SEQUENCE LISTING

<160> NUMBER OF SEQ ID NOS: 2

<210> SEQ ID NO 1
<211> LENGTH: 604
<212> TYPE: PRT
<213> ORGANISM: Artificial Sequence
<220> FEATURE:
<223> OTHER INFORMATION: Human cyclooxygenase 2 (COX2)

<400> SEQUENCE: 1

Met Leu Ala Arg Ala Leu Leu Cys Ala Val Leu Ala Leu Ser His
1               5                   10                  15

Thr Ala Asn Pro Cys Cys Ser His Pro Cys Gln Asn Arg Gly Val Cys
                20                  25                  30

Met Ser Val Gly Phe Asp Gln Tyr Lys Cys Asp Cys Thr Arg Thr Gly
            35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125

Ser Asn Leu Ser Tyr Tyr Thr Arg Ala Leu Pro Pro Val Pro Asp Asp
    130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
        195                 200                 205

Gly Leu Gly His Gly Val Asp Leu Asn His Ile Tyr Gly Glu Thr Leu
    210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
    290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn

```
            355                 360                 365

Thr Leu Tyr His Trp His Pro Leu Leu Pro Asp Thr Phe Gln Ile His
    370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
            420                 425                 430

Val Ser Gln Ala Ser Ile Asp Gln Ser Arg Gln Met Lys Tyr Gln Ser
            435                 440                 445

Phe Asn Glu Tyr Arg Lys Arg Phe Met Leu Lys Pro Tyr Glu Ser Phe
        450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
            515                 520                 525

Ala Tyr Trp Lys Pro Ser Thr Phe Gly Gly Glu Val Gly Phe Gln Ile
            530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
            595                 600

<210> SEQ ID NO 2
<211> LENGTH: 11
<212> TYPE: PRT
<213> ORGANISM: Artificial Sequence
<220> FEATURE:
<223> OTHER INFORMATION: Epitope for S565 acetylated COX2
<220> FEATURE:
<221> NAME/KEY: MISC_FEATURE
<222> LOCATION: (6)
<223> OTHER INFORMATION: The X at position 6 is acetylated serine

<400> SEQUENCE: 2

Gly Cys Pro Phe Thr Xaa Phe Ser Val Pro Asp
1               5                   10
```

COMPOSITION FOR DIAGNOSIS OF DEGENERATIVE NEUROLOGICAL DISEASES

CROSS-REFERENCE TO RELATED APPLICATIONS

This application is a § 371 national phase of International Application No. PCT/KR2019/003284, filed on Mar. 21, 2019, which claims the benefit of Korean Patent Application Nos. 10-2018-0032669, filed on Mar. 21, 2018, and 10-2018-0127656, filed on Oct. 24, 2018, which applications are incorporated by reference herein.

TECHNICAL FIELD

This application claims priority to Korean Patent Application No. 10-2018-0032669 filed on Mar. 21, 2018 and Korean Patent Application No. 10-2018-0127656 filed on Oct. 24, 2018, and the entire specification is a reference of this application.

The present invention relates to a composition for diagnosis of degenerative neurological diseases and, more specifically, to a composition for diagnosis of degenerative neurological diseases, comprising an agent for measuring the level of acetylation of COX2.

BACKGROUND ART

Alzheimer's disease (hereinafter referred to as 'AD') is the most common form of dementia, characterized by accumulation of intracellular neurofibrillary tangles consisting of extracellular amyloid plaques and aggregated amyloid β (Aβ), resulting in cognitive impairment and dementia symptom. In addition to these features, dysregulation of neutroglia cells (particularly, microglia), which are generally closely related to Aβ, is also observed.

In the brain of a patient with degenerative neurological diseases such as AD, microglia with a lost function may respond to accumulation of Aβ and/or secrete pro-inflammatory cytokines by reduced Aβ phagocytosis to be involved in the progression of the diseases. The function loss of the microglia also causes a chronic inflammatory response. The resolution of such an inflammatory response is in a final stage of the inflammatory response, and the inflammatory response may be resolved by neuroinflammatory resolution factor called specialized proresolving mediators (SPMs) including Lipoxin A4 (LxA4), Resolvin E1 (RvE1) and Resolvin D1 (RvD1). This is biased from an M1 phenotype to M2, resulting in recovering the functions of the neuroglia cells, such as conversion to an activated phenotype, downregulation of pro-inflammatory cytokines, and removal of apoptotic cells and debris. According to a recent study, it has been reported that the function of resolving the inflammatory response (SPMs) in AD patients is impaired.

Sphingosine kinases (hereinafter referred to as 'SphK') 1 and 2 are core enzymes involved in the conversion of sphingosine to sphingosine-1-phosphate (S1P), a bioactive lipid which has been known to regulate the inflammatory response. Recently, the role of SphK in the inflammatory response has become the subject of research on various diseases (asthma, rheumatoid arthritis, etc.). However, the role of SphK in the neuroinflammatory response in the brain of AD patients has not been sufficiently studied.

DETAILED DESCRIPTION OF THE INVENTION

Technical Problem

Accordingly, the present inventors made many efforts to find the role of SphK1 in degenerative neurological diseases, and as a result, found that SphK1 was exhibited by increasing the acetylation of cyclooxygenase 2 (COX2) to promote the secretion of neuroinflammatory resolution factor and resulting in inducing the conversion to M2-like phenotype of microglia. In addition, the present inventors confirmed that when the SphK1 was increased in the brain of AD, the acetylation of COX2 was increased, and as a result, Aβ phagocytosis through neuroglia cells was improved, thereby improving cognitive impairment. Furthermore, the present inventors found that the acetylation of COX2 was decreased in microglia and monocytes of an Alzheimer's animal model, which was exhibited at serine 565 of a COX2 protein, and completed the present invention.

Therefore, an object of the present invention is to provide a composition for diagnosis of degenerative neurological diseases, comprising an agent for measuring the level of acetylation of cyclooxygenase-2 (COX2).

Another object of the present invention is to provide a kit for diagnosis of degenerative neurological diseases, comprising an agent for measuring the level of acetylation of cyclooxygenase-2 (COX2).

Yet another object of the present invention is to provide a method for providing information for diagnosis of degenerative neurological diseases, comprising: (a) providing a biological sample from a patient suspected of degenerative neurological diseases; (b) measuring the level of acetylation of COX2 in the sample; and (c) diagnosing degenerative neurological diseases when the level of acetylation of the COX2 is lower than that of a normal control sample.

Technical Solution

In order to achieve an object of the present invention, the present invention provides a composition for diagnosis of degenerative neurological diseases, comprising an agent for measuring the level of acetylation of cyclooxygenase-2 (COX2).

In order to achieve another object of the present invention, the present invention provides a kit for diagnosis of degenerative neurological diseases, comprising an agent for measuring the level of acetylation of cyclooxygenase-2 (COX2).

In order to achieve yet another object of the present invention, the present invention provides a method for providing information for diagnosis of degenerative neurological diseases, comprising: (a) providing a biological sample from a patient suspected of degenerative neurological diseases; (b) measuring the level of acetylation of COX2 in the sample; and (c) diagnosing degenerative neurological diseases when the level of acetylation of the COX2 is lower than that of a normal control sample.

Hereinafter, the present invention will be described in more detail.

The present invention provides a composition for diagnosis of degenerative neurological diseases, comprising an agent for measuring the level of acetylation of cyclooxygenase-2 (COX2).

According to an embodiment of the present invention, nerve cells isolated from an Alzheimer's animal model were treated with [$^{14}$C] acetyl-CoA and COX2 was purified to analyze the level of acetylation. As a result, compared with wild-type mice, it was confirmed that a low level of COX2 acetylation was shown in the nerve cells of the Alzheimer's animal model, and the acetylation of COX2 was increased in the nerve cells of wild-type mice.

Meanwhile, according to another embodiment of the present invention, the acetylation of COX2 in the nerve cells is mediated by SphK1, and it was confirmed that when the expression of SphK1 is lowered, the COX2 acetylation and the secretion of neuroinflammatory resolution factor for resolving the inflammatory response were reduced and thus, abnormal inflammatory responses occur to show Alzheimer-like lesions. On the other hand, it has been confirmed that when the expression of SphK1 is increased, the COX2 acetylation and the secretion of the neuroinflammatory resolution factor for resolving inflammatory responses were increased in the nerve cells, and the functions of microglia are recovered and the resulting Aβ phagocytosis is improved, and as a result, the Alzheimer-like lesions are relieved.

In addition, according to another embodiment of the present invention, it was confirmed that the acetylation of COX2 by SphK1 was shown at serine 565 (S565) of an amino acid sequence of COX2.

Based on these test results, the present inventors have determined that whether COX2 is acetylated, and preferably, whether the COX2 is acetylated at serine (S565) as an amino acid 565 of COX2, will be usefully used for diagnosis of degenerative neurological diseases.

Thus, in one embodiment of the present invention, the present inventors prepared an antibody of specifically binding to COX2 acetylated at serine 565 and then confirmed whether to acetylate COX2 expressed in microgila isolated from the brain and monocytes isolated from the blood in the an Alzheimer's animal model through immunofluorescence staining and Western blotting, and as a result, confirmed that the acetylation of COX2 at serine 565 was significantly reduced in the microgila and the monocytes in the Alzheimer's animal model as compared to that of the wild-type animal.

In addition, according to another embodiment of the present invention, it was confirmed that when the microglia were treated with amyloid β to create a neuroinflammatory environment, the acetylation of COX2 at serine 565 (S565) was significantly lowered compared to when the microglia were not treated with amyloid β.

Accordingly, an agent capable of measuring the level of acetylation of COX2, preferably, an agent capable of measuring the level of acetylation of serine (S565), which is an amino acid 565 among amino acids constituting the COX2 protein, may be very useful used for diagnosis of degenerative neurological diseases.

In the present invention, the amino acid sequence of COX2 may be confirmed through GeneBank accession No. AAR23927.1, No. AAA58433.1, No. AAA57317.1, etc., and more specifically, may consist of the following amino acid sequence represented by SEQ ID NO: 1.

```
                                      SEQ ID NO: 1
mlaralllca vlalshtanp ccshpcqnrg vcmsvgfdqy kcdctrtgfy gencstpefl triklflkpt pntvhyilth fkgfwnvvnn ipflrnaims yvltsrshli dspptynady gyksweafsn lsyytralpp vpddcptplg vkgkkqlpds neivekllr rkfipdpqgs nmmfaffaqh fthqffktdh
```

-continued
```
krgpaftngl ghgvdlnhiy getlarqrkl rlfkdgkmky qiidgemypp tvkdtqaemi yppqvpehlr favgqevfgl vpglmmyati wlrehnrvcd vlkqehpewg deqlfqtsrl iligetikiv iedyvqhlsg yhfklkfdpe llfnkqfqyq nriaaefntl yhwhpllpdt fqihdqkyny qqfiynnsil lehgitqfve sftrqiagrv aggrnvppav qkvsqasidq srqmkyqsfn eyrkrfmlkp yesfeeltge kemsaeleal ygdidavely pallvekprp daifgetmve vgapfslkgl mgnvicspay wkpstfggev gfqiintasi qslicnnvkg cpftsfsvpd peliktvtin asssrsgldd inptvllker stel
```

In the present invention, the agent for measuring the level of acetylation of COX2 may be an antibody specific to the acetylated COX2, a fragment of the antibody, or an aptamer.

The antibody refers to an immunoglobulin that specifically binds to an antigenic site. The antibody in the present invention does not bind to non-acetylated COX2 and other proteins in addition to the acetylated COX2. Preferably, the antibody in the present invention may be an antibody that does not bind to COX2 in which an amino acid at another position is acetylated in addition to the COX2 acetylated at serine 565.

The antibody may be prepared by cloning a gene of COX2 acetylated at serine 565 into an expression vector to obtain a protein encoded by the gene, and from the obtained protein by a general method in the art.

Alternatively, an acetylated COX2 protein-specific antibody may also be prepared using a fragment of a protein containing an epitope site of COX2 acetylated at serine 565.

The form of the antibody of the present invention is not particularly limited, and includes a polyclonal antibody or a monoclonal antibody. In addition, as long as any antibody has antigen-antibody binding, a part of the whole antibody is also included in the antibody of the present invention, and all kinds of immunoglobulin antibodies that specifically bind to the acetylated COX2 are included. For example, not only antibodies in complete form having two full-length light chains and two full-length heavy chains, but also functional fragments of antibody molecules, i.e., Fab, F(ab'), F(ab')2, and Fv having an antigen-binding function are included. Further, the antibody of the present invention also includes special antibodies such as humanized antibodies and chimeric antibodies and recombinant antibodies as long as any antibody may specifically bind to the acetylated COX2 protein.

Most preferably, the antibody may be an antibody that specifically binds to an epitope comprising an amino acid sequence of SEQ ID NO: 2 or an amino acid sequence having 80% or more sequence identity thereto. The amino acid sequence of SEQ ID NO: 2 is a peptide fragment including acetylation of serine 565 in the COX2 protein represented by SEQ ID NO: 1, and the antibody of the present invention may be an antibody specifically binding to an epitope containing an amino acid sequence having 80% or more sequence identity, preferably 85% or more sequence identity, more preferably 90% or more sequence identity, most preferably 95% or more sequence identity to SEQ ID NO: 2.

In one embodiment of the present invention, the present inventors prepared an antibody recognizing a peptide consisting of an amino acid sequence of SEQ ID NO: 2, that is, a peptide acetylated at serine 565 as a peptide consisting of amino acids 560 to 570 of the COX2 protein represented by SEQ ID NO: 1. The present inventors confirmed that the antibody bound to the COX2 acetylated at serine 565, but did not bind to COX2 where serine 565 was not acetylated to confirm the specificity of the antibody and the usefulness of the epitope.

In the present invention, the aptamer refers to a single-stranded DNA (ssDNA) or RNA having high specificity and affinity for a specific substance. The aptamer has very high affinity to a specific substance, is stable, may be synthesized by a relatively simple method, can be variously modified to increase a binding force, and can be a target substance even for cells, proteins, and small organic substances, and thus has very high specificity and stability thereof compared to already developed antibodies. In the present invention, the aptamer is not particularly limited in its kind and form as long as any aptamer can bind to acetylated COX2.

In the present invention, the degenerative neurological disease may be at least one selected from the group consisting of Alzheimer's disease, Parkinson's disease, progressive supranuclear palsy, multi-system atrophy, olivopontocerebellar atrophy, Shire-Dragger syndrome, striatonigral degeneration, Huntington's disease, amyotrophic lateral sclerosis (ALS), essential tremor, corticobasal degeneration, diffuse Lewy body disease, Parkin's-ALS-dementia complex, Niemann-Pick disease, Pick disease, cerebral ischemia, and cerebral infarction, but is not limited thereto.

Further, the present invention provides a kit for diagnosis of degenerative neurological diseases, comprising an agent for measuring the level of acetylation of COX2.

The diagnostic kit of the present invention includes one or more other constituent compositions suitable for analysis methods, solutions or devices as well as an antibody, an antibody fragment, or an aptamer that selectively recognizes acetylated COX2 as a marker selectively to measure the level of acetylation of COX2.

More specifically, the kit may be a diagnostic kit comprising essential elements required for performing Western blotting, immunofluorescence staining, ELISA, and the like. These kits include an antibody specific to the acetylated COX2 protein. The antibody is an antibody with high specificity and affinity to the acetylated COX2 protein and little cross-reactivity with other proteins, and is a monoclonal antibody, a polyclonal antibody or a recombinant antibody. In addition, these kits may include antibodies specific to a control protein. In addition, the kit may include reagents capable of detecting bound antibodies, e.g., labeled secondary antibodies, chromophores, enzymes (as conjugated with antibodies), and other substances capable of binding to substances or antibodies thereof. In addition, the kit of the present invention may include a washing solution or an eluent capable of removing substrates for color development reaction with an enzyme, unbound proteins, etc., and retaining only the bound protein marker.

In addition, the kit of the present invention may further include an antibody, a fragment of the antibody, or an aptamer capable of binding to both non-acetylated and acetylated COX2 proteins. In this case, the kit of the present invention may more accurately diagnose degenerative neurological diseases by checking a ratio of the level of the acetylated COX2 to the expression level of total COX2.

The present invention provides a method for providing information for diagnosis of degenerative neurological diseases, comprising: (a) providing a biological sample from a patient suspected of degenerative neurological diseases; (b) measuring the level of acetylation of COX2 in the sample; and (c) diagnosing degenerative neurological diseases when the level of acetylation of the COX2 is lower than that of a normal control sample.

The present inventors first found that the acetylated COX2 may function as a diagnostic marker for degenerative neurological diseases, and thus, the present invention provides a method for providing information required for diagnosis of degenerative neurological diseases by measuring the level of acetylation of COX2.

In the present invention, the biological sample in step (a) may be selected from the group consisting of blood, blood cells, brain tissue, nerve cells, cerebrospinal fluid, saliva, nasal fluid, sputum, synovial fluid, amniotic fluid, ascites, cervical or vaginal secretions, and urine, but is not limited thereto, and may be preferably selected from the group consisting of blood, blood cells, brain tissue, nerve cells, and cerebrospinal fluid.

According to an embodiment of the present invention, even in monocytes isolated from the blood as well as microglia isolated from the brain tissue in the Alzheimer's animal model, it was confirmed that the level of acetylation of COX2 at serine 565 was significantly lowered compared to the wild-type mice. This result means that degenerative neurological diseases may be diagnosed non-invasively even through the blood, and thus, it is a very surprising discovery.

The method of measuring the level of acetylation of COX2 in step (b) of the present invention may be selected from the group consisting of autoradiography, liquid scintillation counting, molecular weight assay, liquid chromatographic mass assay, Western blot, ELISA, radioimmunoassay, radioimmunodiffusion, Ouchterlony immunodiffusion, rocket immunoelectrophoresis, immunofluorescence staining, immunohistochemical staining, immunoprecipitation assay, complement fixation assay, FACS, and protein chip, but is not limited thereto.

In one embodiment of the present invention, a COX2 protein of nerve cells reacted in the presence of [$^{14}$C] acetyl-CoA was isolated using an immunoprecipitation method, and then the level of acetylation of COX2 was evaluated using a liquid scintillation counting method with respect to [$^{14}$C], or the level of acetylation of COX2 was analyzed by immunofluorescence staining and Western blot in the brain tissue or microglia of the Alzheimer's animal model using an antibody that specifically binds to the COX2 protein acetylated at serine 565.

In step (c) of the present invention, the level of acetylation of COX2 of a subject measured by the method of step (b) is compared with the level of acetylation of COX2 of a normal person measured by the same method. A subject of which the level of acetylation of COX2 is decreased compared to that of a healthy normal person may be determined to have degenerative neurological diseases.

In step (c), the level of acetylation of COX2 may be quantified and compared as (expression level of acetylated COX2/expression level of total COX2).

On the other hand, according to an embodiment of the present invention, it was confirmed that the acetylation of COX2 and the secretion of neuroinflammatory resolution factor were significantly reduced in the nerve cells exposed to the Alzheimer's animal or the neuroinflammatory environment compared to the wild type, and it was confirmed that this phenomenon is closely associated with even the expression level of SphK1.

Therefore, the level of acetylation of COX2 was measured in a biological sample obtained from a patient suspected of degenerative neurological diseases, and the expression level of mRNA or protein of SphK1 was additionally measured in the same sample, As a result, if the level of acetylation of COX2 and the expression level of mRNA or protein of SphK1 are decreased compared to those in a normal control, it is possible to more accurately diagnose that degenerative neurological diseases are progressing in the corresponding patient.

In this case, the expression level of mRNA of SphK1 may be measured by using quantitative or semi-quantitative RT-PCR, quantitative or semi-quantitative real-time RT-PCR, Northern blot, DNA or RNA chip, etc. The expression level of the SphK1 protein may be measured by using Western blot, ELISA, radioimmunoassay, radioimmunodiffusion, Ouchterlony immunodiffusion, rocket immunoelectrophoresis, immunohistochemical staining, immunoprecipitation assay, complement fixation assay, FACS, protein chip, etc., but the present invention is not limited thereto.

In addition, in the biological sample obtained from the patient suspected of degenerative neurological diseases, if it was further confirmed that the expression of mRNA or protein of SphK1 and the acetylation of COX2 were decreased and the amount of secretion of the neuroinflammatory resolution factor was decreased, it is possible to more accurately determine whether the degenerative neurological diseases are progressing.

Advantageous Effects

According to the present invention, since the acetylation of COX2 in degenerative neurological diseases is significantly reduced, whether COX2 is acetylated may be utilized as a diagnostic marker for degenerative neurological diseases, and it is possible to diagnose degenerative neurological diseases more rapidly and accurately by using same.

BRIEF DESCRIPTION OF THE DRAWINGS

FIGS. 1a and 1b illustrate results of evaluating binding (a) and dissociation (b) of SphK1 and acetyl-CoA.

FIG. 1c illustrates a result of evaluating acetylation of COX2 in the presence of SphK1, acetyl-CoA, and sphingosine ([$^{14}$C] aspirin-treated test group is set as a positive control).

FIG. 1d illustrates a result of confirming changes in molecular weight by acetylation of COX2 in the presence of SphK1, acetyl-CoA and/or sphingosine using LC-MS/MS.

FIG. 1e illustrates a result of confirming that acetylation of COX2 at a residue S565 occurs in the presence of SphK1, acetyl-CoA and/or sphingosine using LC-MS/MS.

FIG. 1f illustrates a result of confirming that the acetylation does not occur well when S565 of a COX2 protein is mutated.

FIG. 2a illustrates a result of evaluating the expression of SphK1 and SphK2 when SphK1 siRNA has been treated to wild-type (WT) nerve cells.

FIG. 2b illustrates a result of confirming the acetylation of a COX2 protein when SphK1 siRNA has been treated in nerve cells [$^{14}$C] aspirin-treated wild-type nerve cells are set as a positive control).

FIG. 2c illustrates a result of confirming the secretion of neuroinflammatory resolution factor (SPMs) such as LxA4, RvE1, and RvD1 when SphK1 siRNA has been treated in nerve cells.

FIG. 2d illustrates a result of confirming the secretion of 15-R-LxA4 using LC-MS/MS when SphK1 siRNA has been treated in nerve cells.

FIG. 3a illustrates a result of performing an acetylation assay of a COX2 protein in nerve cells derived from wild-type, APP/PS1, APP/PS1/SphK1 tg, and SphK1 tg mice. [$^{14}$C] asprine-treated nerve cells have been set as a positive control.

FIG. 3b illustrates a result of measuring protein amounts of LxA4 and RvE1 in CM of nerve cells derived from wild-type, APP/PS1, APP/PS1/SphK1 tg, and SphK1 tg mice.

FIG. 3c illustrates a result of specifying an amount of 15-R-LxA4 using LC-MS/MS in nerve cells derived from wild-type, APP/PS1, APP/PS1/SphK1 tg, and SphK1 tg mice.

FIG. 4a illustrates immunofluorescent images (left) of microglia (Iba1) in the brain cortex of wild-type, APP/PS1, APP/PS1/SphK1 tg and SphK1 tg mice and results (right) of quantifying the immunofluorescent images.

FIG. 4b illustrates immunofluorescent images (left) of astrocytes (GFAP) in the brain cortex of mice and results (right) of quantifying the immunofluorescent images.

FIG. 4c illustrates a result of evaluating mRNA expression levels of inflammatory markers M1 and M2 in the brain of mice (Marker M1: TNF-a, IL-1b, IL-6 and iNOS, Immunomodulatory factor: IL10, Marker M2: IL-4, TGF-b and Arg1).

FIG. 5a illustrates a result of confirming microglia around Aβ plaques in the brain cortex of APP/PS1 and APP/PS1/SphK1 tg mice.

FIG. 5b illustrates a result of confirming the phagocytic ability of microglia in the brain cortex of wild-type, APP/PS1, APP/PS1/SphK1 tg and SphK1 tg mice.

FIG. 5c illustrates a result of confirming that Aβ plaques are digested within lysosomes of microglia in the brain cortex of APP/PS1 and APP/PS1/SphK1 tg mice.

FIGS. 5d and 5e illustrate results of confirming the expression of Aβ degrading enzymes NEP, MMP9 and IDE and a phagocytic marker CD36 in microglia of wild-type, APP/PS1, APP/PS1/SphK1 tg, and SphK1 tg mice.

FIG. 5f illustrates a result of confirming sizes of Aβ plaques where phagocytosis occurs in the brain cortex of APP/PS1 and APP/PS1/SphK1 tg mice.

FIG. 6a illustrates a diagram (left) showing immunofluorescence staining of thioflavin S (ThioS, Aβ plaques) in the brain medulla and hippocampus of APP/PS1 and APP/PS1/SphK1 tg mice and a result (right) of quantifying areas occupied by Aβ plaques (n=6/group).

FIGS. 6b and 6c illustrate results of analyzing the accumulation of A1340 and A1342 in the mouse's brain by immunofluorescence staining (b) or an ELISA kit (c).

FIG. 6d illustrates a result of quantifying vasculopathy.

FIG. 6e illustrates a result of quantifying a tau protein.

FIGS. 6f to 6i illustrate results of showing immunofluorescence staining and quantification of synaptophysin (f), MAP2 (g), synapsin 1 (h) or PSD95 (i) in the brain cortex of each animal group.

FIG. 7a illustrates a result of evaluating learning and memory through a Morris Water Maze test of wild-type (n=14), APP/PS1 (n=12), APP/PS1/SphK1 tg (n=12), and SphK1 tg (n=13) mice.

FIGS. 7b to 7d illustrate results of measuring time spent in a target platform on day 11 (b), measuring time spent in other quadrants (c), and measuring a path length, a swim speed, and the number of times when each animal enters a small target area for 60 seconds (d).

FIG. 7e illustrates a swim path on day 10 of the test.

FIG. 7f illustrates a result of contextual and tone tasks during a fear conditioning test.

FIG. 7g illustrates a result of showing time spent on a wall side and a center region during an open field test and a ratio of the center region.

FIG. 7h illustrates movement paths of mice during the open field test.

FIG. 8a is a diagram illustrating a chemical structure of a COX2 acetylating agent.

FIG. 8b illustrates a result of confirming the secretion of neuroinflammatory resolution factor (SPMs) by treating a COX2 acetylating agent.

FIG. 8c illustrates a result of confirming that N-acetyl sphingosine causes COX2 acetylation.

FIG. 8d illustrates a result of confirming that acetylation of COX2 at a residue S565 occurs in the presence of N-acetyl sphingosine using LC-MS/MS.

FIG. 9a illustrates immunofluorescence images (left) of microglia (Iba1) in the brain cortex of wild-type, APP/PS1, and APP/PS1 mice injected with N-acetyl sphingosine, FTY720 (sphingosine derivative) and S1P and results (right) of quantifying the immunofluorescence images.

FIG. 9b illustrates immunofluorescence images (left) of astrocytes (GFAP) in the brain cortex of mice and results (right) of quantifying the immunofluorescence images.

FIG. 9c is a diagram (top) illustrating immunofluorescence staining of Thioflavin S (ThioS, Aβ plaques) in the brain medulla and hippocampus of APP/PS1 and APP/PS1 mice injected with N-acetyl sphingosine, FTY720 (sphingosine derivative) and S1P and illustrates a result (bottom) of quantifying areas occupied by Aβ.

FIG. 9d illustrates a result of evaluating learning and memory of wide-type, APP/PS1, and APP/PS1 mice injected with N-acetyl sphingosine, FTY720 (sphingosine derivative) and S1P through a Morris Water Maze test.

MODE FOR CARRYING OUT INVENTION

Figure 1A:
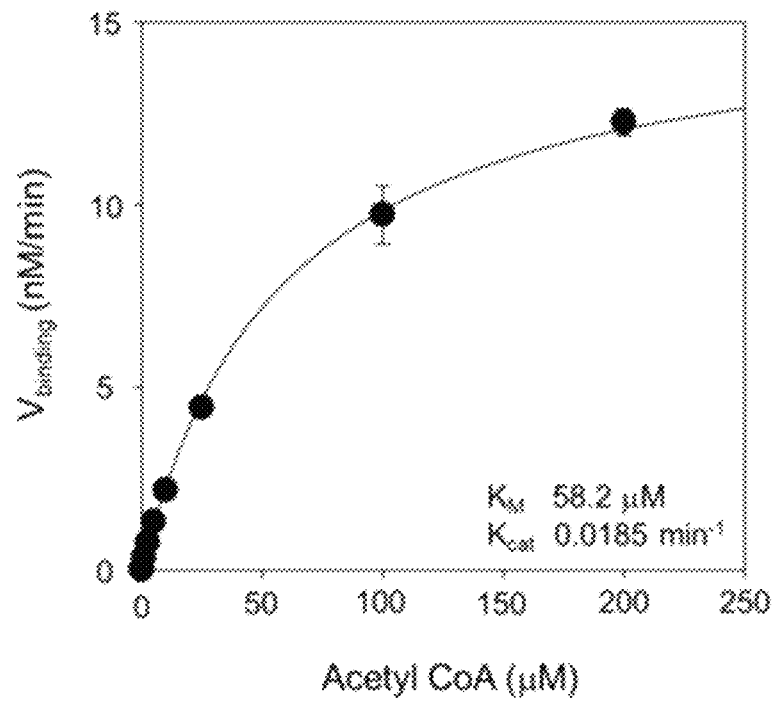
FIGS. 1a to 1f illustrate results of showing that SphK1 acetylates S565 of COX2 as an acetyltransferase.

Hereinafter, the present invention will be described in detail.

However, the following Examples are just illustrative of the present invention, and the contents of the present invention are not limited to the following Examples.

Experiment Method

1. Mouse

A mouse test was approved by the Kyungpook National University Institutional Animal Care and Use Committee (IACUC). Based on C57BL/6 mice (Charles River, UK), a transgenic mouse line overexpressing APPswe (hAPP695swe) or PS1 (presenilin-1M146V) was used [hereinafter, APP mouse: mouse overexpressing APPswe, PS1 mouse: mouse overexpressing presenilin-1M146V; GlaxoSmithKline]

SphK1 tg (SphK1 gene overexpressing mice) was crossed with APP mice and APP/PS1 mice to prepare APP/PS1/SphK1 tg mice.

2. Isolation of Monocytes into Mouse Blood

After the blood from a mouse was collected through heart blood collection, ammonium chloride was added in an amount equal to 10 times of the amount of the collected blood to dissolve red blood cells in the blood. The blood from which the red blood cells were dissolved was centrifuged to remove a supernatant, and then monocytes were isolated.

3. Preparation of ac-S565 Antibody

In order to prepare an antibody capable of detecting whether serine 565 (S565) of a COX2 protein of SEQ ID NO: 1 was acetylated, a peptide of a N-GCPFTS$^{ac}$FSVPD-C sequence represented by SEQ ID NO: 2 was prepared and conjugated with a carrier protein (keyhole limpet hemocyanin), and then the prepared peptide was immunized to rabbits according to an immune progression table shown in Table 1 below to prepare a rabbit polyclonal antibody.

TABLE 1

|  |  |
|---|---|
| Day −1 | Pre-immune serum collection |
| Day 0 | Primary immunization |
| Day 14 | 1st boost |
| Day 21 | Test beleed and ELISA test |
| Day 35 | 2nd boost |
| Day 42 | Product on bleed |
| Day 56 | 3rd boost |
| Day 63 | Production bleed |
| Day 77 | ELISA |

Time
Step

4. Treatment of SphK siRNA

SphK1 siRNA (Dharmacon SMART pool) and a siRNA control (Dharmacon) were treated on nerve cells of E18 C57BL/6 mice for 48 hours. The nerve cells were collected and the acetylation and neuroinflammatory resolution factor were analyzed.

5. Immunofluorescence

After the cerebrum and the hippocampus of a mouse were immobilized, anti-20G10 against amyloid-β (Aβ) 42 (mouse, 1:1000) and anti-G30 against Aβ 40 (rabbit, 1:1000), anti-MAP2 (chicken, 1:2000), anti-Synaptophysin (mouse, 1:100), anti-Synapsin1 (rabbit, 1:500), anti-PSD95 (mouse, 1:100), anti-Iba-1 (rabbit, 1:500), and anti-GFAP (rabbit, 1:500) were incubated together. The sites were analyzed using a confocal laser scanning microscope or an Olympus BX51 microscope equipped with Fluoview SV1000 imaging software (Olympus FV1000, Japan). Percentages of areas of the stained sites to an area of total tissues were quantified using Metamorph software (Molecular Devices).

In addition, cerebral tissues of wild-type and APP/PS1 9-month-old mice and human-derived microglia were incubated together with anti-ac-S565 (rabbit, 1:100), anti-COX2 (mouse, 1:500, Thermo Fisher Scientific), and anti-Iba1 (goat, 1:500, Abcam). In the cerebral tissues and the human-derived microglia, percentages of cells stained with anti-ac-S565, anti-COX2 and anti-Iba1 among cells stained with anti-COX2 and anti-Iba1 were quantified and analyzed using MetaMorph (Molecular Devices, USA).

6. Quantitative Real-Time PCR

RNA was extracted according to a manufacturer's manual using a commercially available RNeasy kit (QIAGEN). cDNA was synthesized from 5 µg of total RNA using a commercially available cDNA kit (Takara Bio Inc.). Quantitative real-time PCR was performed using a Corbett research RG-6000 real-time PCR instrument.

7. Western Blot

The expression of the proteins was analyzed using Western blotting. First, antibodies against CD36 (Novus biolobicals) and β-actin (Santa Cruz) were used, and densitometric quantification was performed using ImageJ software (US National Institutes of Health).

In addition, a Western blot sample was prepared by reacting a recombinant COX2 protein with aspirin and N-acetyl sphingosine (Sigma, 01912, N-AS). In addition, microglia were isolated from the cerebra of wild-type and APP/PS1 9-month-old mice to prepare a Western blot sample, and microglia (Applied Biologics Materials, USA) were incubated with amyloid beta, and then a Western blot sample was prepared. The prepared Western blot sample was subjected to electrophoresis on a polyacrylamide gel to isolate proteins, transferred to a nitrocellulose filter, and then bound with anti-ac-S565 (rabbit, 1:500), anti-COX2 (rabbit, 1:1,000, Abcam), and anti-actin (mouse, 1:1,000, Santa Cruz) antibodies, and then bands were shaped using secondary antibodies, and quantified and analyzed using ImageJ (National Institutes of Health, USA).

8. Immunoenzyme Assay

A commercially available ELISA kit (Biosource) was used, and the hemispheres of mice were homogenized and added in a buffer containing 0.02 M of guanidine to prepare a sample for Aβ ELISA. In order to measure neuroinflammatory resolution factor, nerve cells from the mouse cerebrum were incubated to prepare conditioned media (CM). Thereafter, according to the manufacturer's manual, ELISA for Aβ and SPM was performed.

9. Behavioral Test

In order to confirm potential effects on learning and memory, Morris water maze (MWM) and fear conditioning tests were performed. In the MWM, the mouse learned a task 4 times a day for 10 days, a platform was removed on day 11, and a probe trial was performed. In the fear conditioning, on day 1, the mouse was added in a conditioning chamber, and sound stimulation (10 kHz, 70 dB) and electrical stimulation (0.3 mA, 1 s) were applied. On day 2, the memory on a space was confirmed without stimulation in the same conditioning chamber as day 1, and on day 3, a memory test for fear was performed when only the sound stimulation was applied in another conditioning chamber. An open field test was performed to evaluate motor ability and immediate activity. In the open field test, the mouse was placed in a quadrangular box for 10 minutes and then overall motor ability and time and distances were measured.

10. Method for Measuring Level of COX2 Acetylation

A COX2 protein of nerve cells reacted for 1 hour at 37° C. in the presence of [$^{14}$C] acetyl-CoA was isolated by immunoprecipitation, and then liquid scintillation counting was performed on [$^{14}$C].

11. Enzymatic Analysis of Acetyltransferase

The acetyl-CoA binding activity of SphK1 was analyzed by filter binding assay in the presence of 10 mM sphingosine. The binding rate (Vbinding) of [$^{3}$H] acetyl-CoA for SphK1 was expressed as an acetyl-CoA concentration. Non-linear regression analysis of a saturation plot showed acetyl-CoA and SphK1 binding activities using $K_{cat}$ (catalyst constant) and $K_M$ (Michaelis-Menten constant).

12. LC-MS/MS

In order to confirm the relationship between the secretion of SphK1 and the secretion of neuroinflammatory resolution factor in nerve cells, the nerve cells were isolated from 9-month-old WT, APP/PS1, APP/PS1/SphK1 tg, and SphK1 tg mice. The nerve cells were sonicated and incubated with 2.5 mM acetyl-CoA (Sigma) (24 hours, 37° C.). In addition, CM was harvested from nerve cells treated with SphK1 siRNA or control siRNA. 200 µl aliquots of each cell lysate or CM were mixed with 100 µg/ml 100 µl of a 15-S-LxA4-d5 (internal standard, Cayman chemical) solution, 100 µl of a 1% formic acid solution, and 600 µl of water, and then added with 4 ml of ethyl acetate. After vortexing and centrifuging (13,200 rpm), the mixture was frozen in a deep freezer for each 10 minutes and 2 hours. An organic supernatant was separated and dried under a nitrogen stream. The remaining solution was reconstituted with a 60% acetonitrile solution injected into an LC-MS/MS system. This sample was subjected to 15-R-LxA4 concentration analysis using an Agilent 6470 Triple Quad LC-MS/MS system (Agilent, Wilmington, DE, USA) connected to an Agilent 1290 HPLC system.

To confirm an acetylation site of COX2, a COX2 enzyme was precipitated with trichroloacetic acid (Merck) and dried. The dried extract was resuspended in 10 μL of a 5 M urea solution, and a 0.1 M ammonium bicarbonate buffer was incubated at 37° C. with 1 μg trypsin (Promega) for 16 hours. Thereafter, the sample was treated with 1 M DTT (GE Healthcare) at room temperature for 1 hour and then alkylated with 1M iodoacetamide (Sigma) for 1 hour. A protein sample was loaded onto a ZORBAX 300SB-C18 column for sequencing. Peptides were identified with BioTools 3.2 SR5 (Bruker Daltonics).

13. Treatment of COX2 Acetylating Agent

In order to measure neuroinflammatory resolution factor, nerve cells from the mouse's cerebrum were incubated and then treated with 10 nM N-acetyl sphingosine 1 phsosphate (Toronto Research chemicals, C262710) and N-acetyl sphingosine (Sigma, 01912) to prepare CM. For COX2 acetylation analysis, nerve cells were incubated from the mouse's cerebrum and treated with 2uCi [$^{14}$C] N-acetyl sphingosine (ARC, ARC1024) and then prepared. In addition, for an in vivo experiment, 5 mg/kg N-acetyl sphingosine (Sigma, 01912), 1 mg/kg FTY720, and 3 uM S1P were injected into 7-month-old APP/PS1 mice daily for 4 weeks through intraperitoneal injection.

14. Statistical Analysis

For comparison of two groups, a T-test of students was performed, while for comparison of multiple groups, repeated measurement analysis of a Tukey's HSD test and a variance test was performed according to an SAS statistical package (release 9.1; SAS Institute Inc., Cary, NC). *$p<0.05$ and **$p<0.01$ were considered to be significant.

Experiment Results

1. SphK1 Induces Acetylation at an S565 Residue of COX2 as an Acetyltransferase.

Figure 1B:
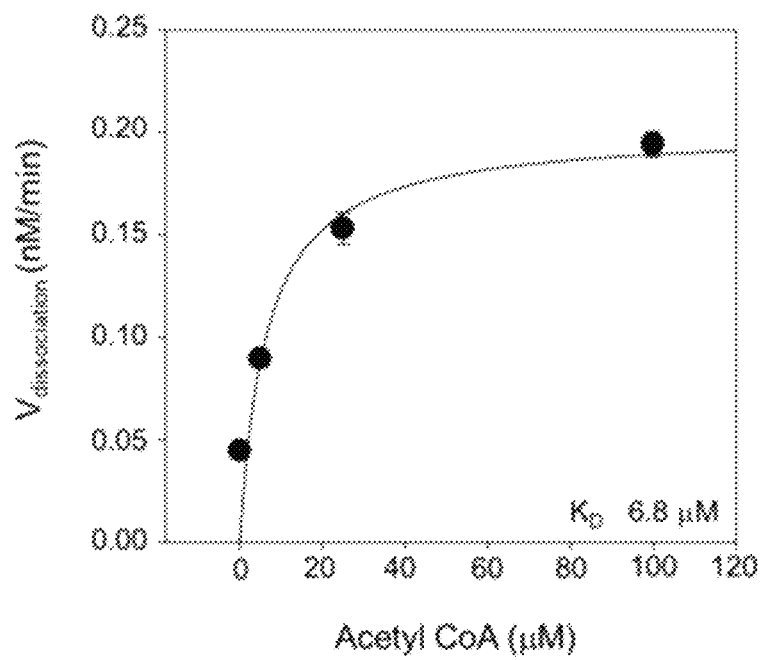

In order to confirm the acetyltransferase activity of SphK1, analysis of binding and dissociation of an acetyl groups from an enzyme was performed. The binding of the acetyl group to SphK1 was saturated as the concentration of acetyl-CoA was increased, and $K_M$ and $K_{cat}$ values were 58.2 μm and 0.0185 min$^{-1}$, respectively (FIG. 1a). After an equilibrium dialysis test, the bound acetyl group was also dissociated from an acetyl-CoA:SphK1 complex in the presence of concentration-dependently competitive free acetyl-CoA. This dissociation of acetyl-CoA and SphK1 was saturated at a high inhibitor concentration and showed a $K_D$ value of 6.8 μm (FIG. 1b). A $K_D$ (i.e., dissociation constant) value lower than a $K_M$ value (i.e., binding affinity) represented acetyltransferase properties of SphK1.

Figure 1C:
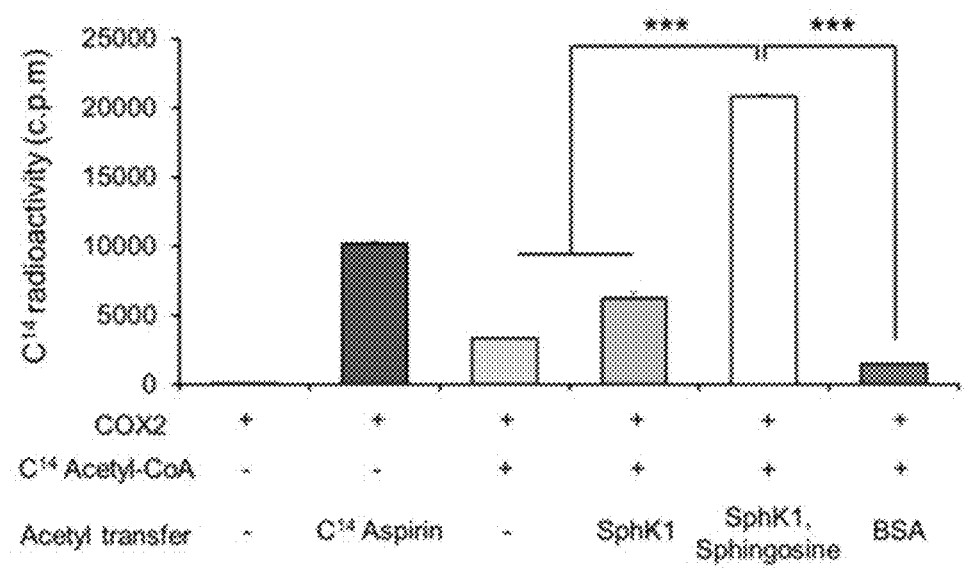

Next, in order to confirm the acetyltransferase activity of SphK1 in relation to COX2, purified SphK1 was incubated with COX2 and [$^{14}$C] acetyl-CoA in the presence or absence of sphingosine to measure the acetylation. In addition, aspirin, known to cause acetylation at a COX2 S516 residue, was used as a positive control to confirm the level of acetylation. Referring to the results of FIG. 1c, it can be seen that SphK1 induces a higher level of acetylation for COX2 than aspirin in the presence of Sphingosine, which indicates that SphK1 exhibits acetyltransferase activity to acetylate COX2 through a sphingosine or sphingosine intermediate (FIG. 1c).

Finally, SphK1, acetyl-CoA and sphingosine were treated to COX2 in order to confirm an acetylation position of COX2 acetylated by SphK1.

Figure 1D:
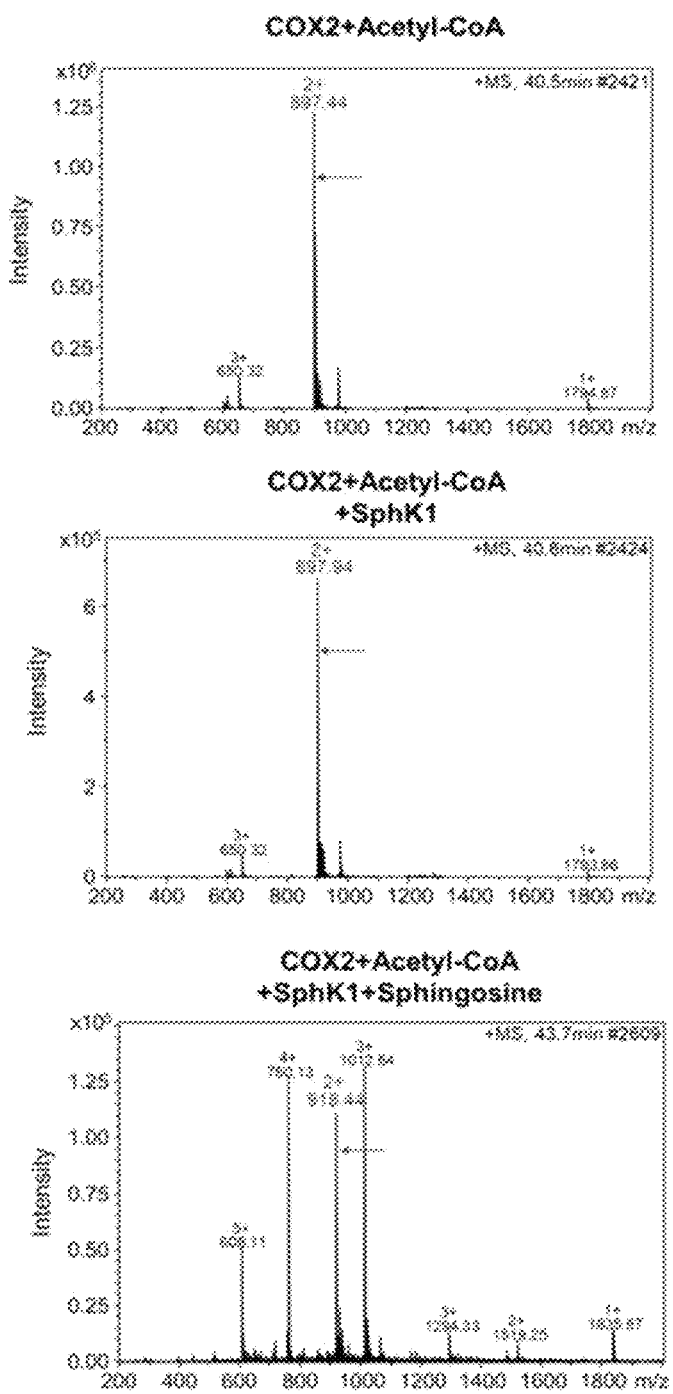
Figure 1E:
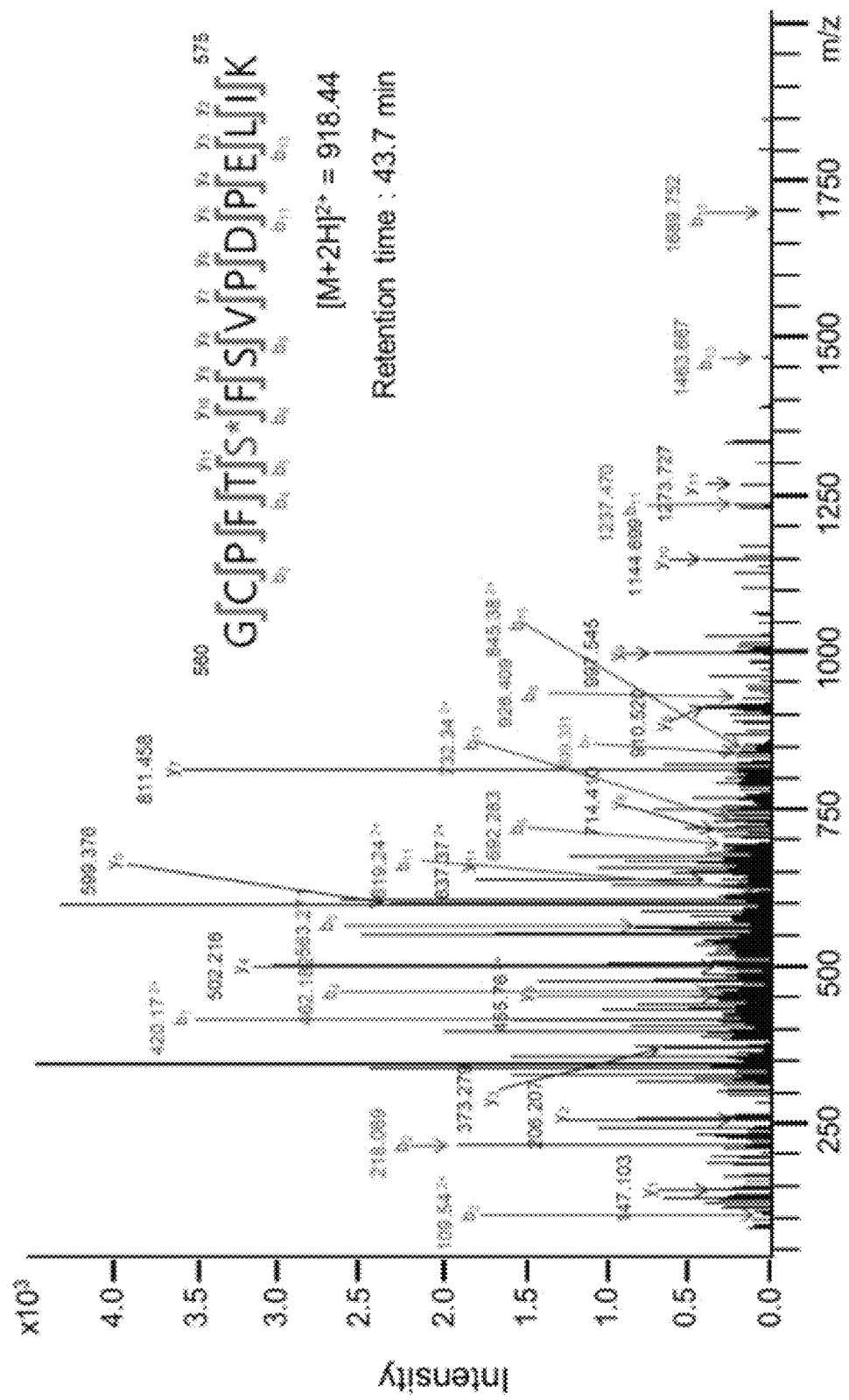
Figure 1F:
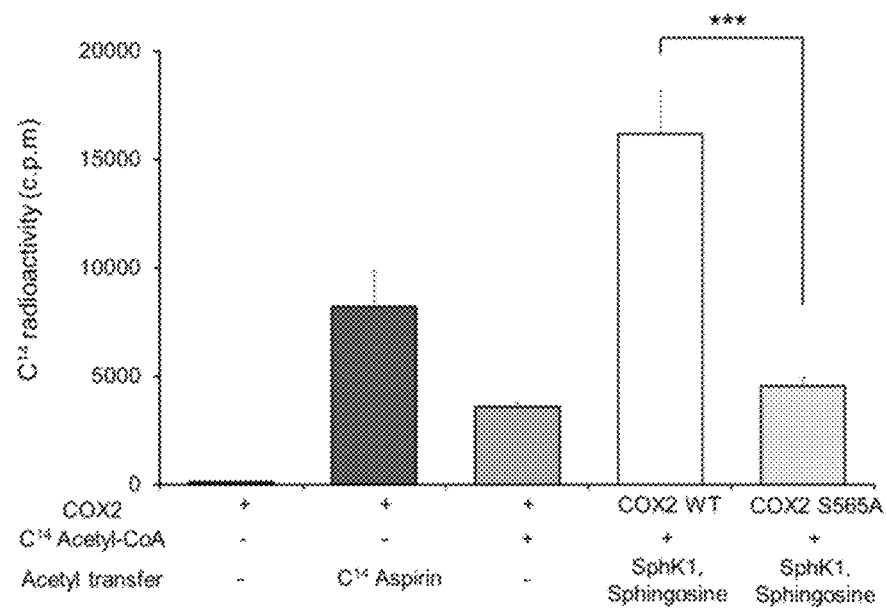

As such, COX2 treated with SphK1, acetyl-CoA and sphingosine had an acetyl group, and COX2 treated without sphingosine had no acetyl group. In addition, it was confirmed that serine 565 (S565) for a peptide 560-GCPFTSFSVPDPELIK-575 of COX2 was acetylated in the presence of SphK1 (FIGS. 1d and 1e). In order to establish its causal relationship, the present inventors mutated S565 of COX2 to an Ala 565 residue (S565A) and then performed acetylation analysis. Wild-type COX2 was acetylated by SphK1 and sphingosine, but S565A-mutated COX2 had reduced acetylation in the presence of SphK1, and these results indicate that S565 of COX2 is a major target site for SphK1-mediated COX2 acetylation (FIG. 1e. In particular, it was confirmed that the position of the acetylation of COX2 S565 by SphK1 was different from the position (S516) acetylated with aspirin.

2. When SphK1 has been Inhibited in Nerve Cells, a Decrease in Secretion of Neuroinflammatory Resolution Factor is Caused by Reduction of COX2 Acetylation.

Figure 2A:
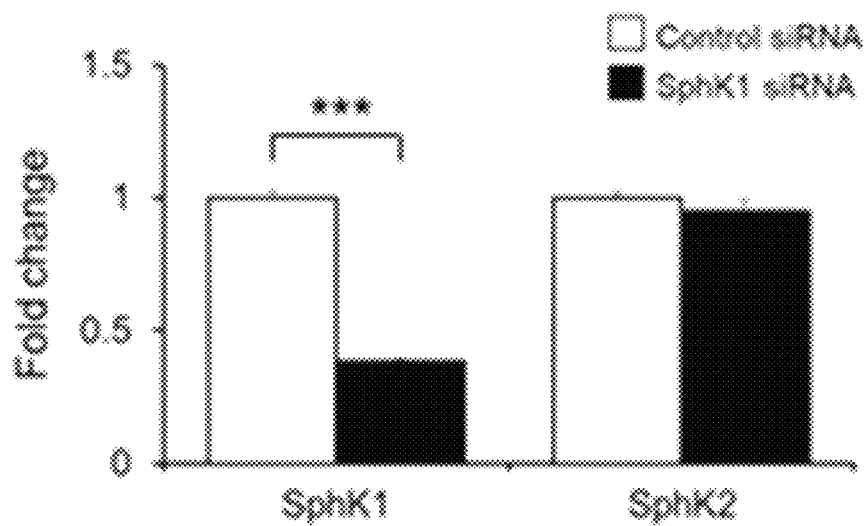
FIGS. 2a to 2d illustrate results of showing that neuroinflammatory resolution factor are decreased by reduction of acetylation of COX2 when SphK1 has been inhibited.
Figure 2B:
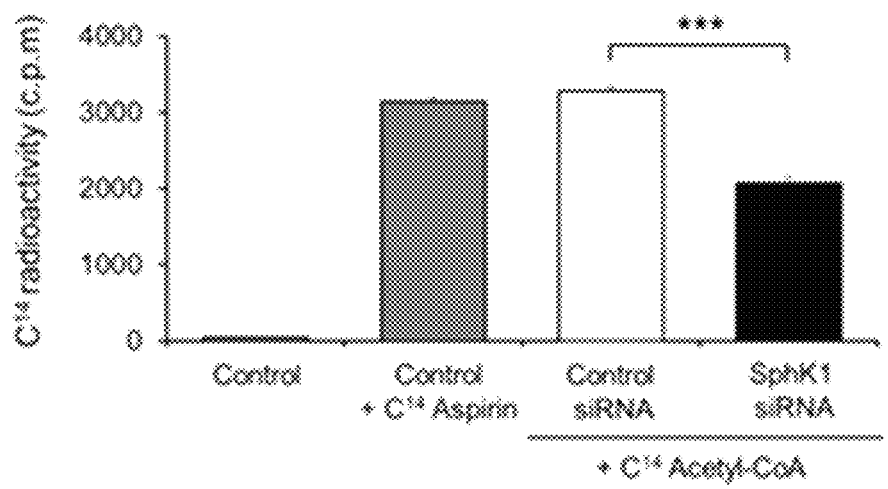

In order to more directly confirm the correlation between SphK1 and COX2 acetylation in nerve cells, wild-type nerve cells were treated with SphK1 siRNA and COX2 acetylation was confirmed. It was confirmed that the COX2 acetylation was reduced in nerve cells treated with SphK1 siRNA (FIG. 2b).

Figure 2C:
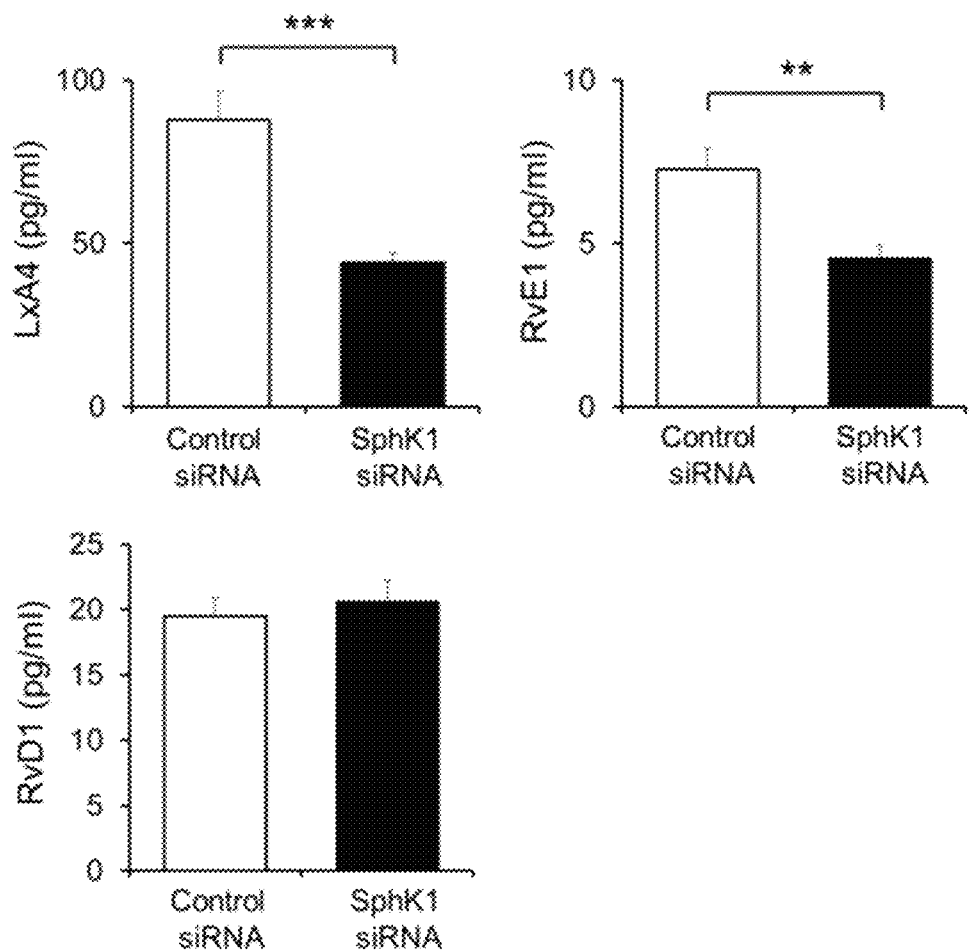

Next, changes in neuroinflammatory resolution factor by COX2 acetylation were observed. It was confirmed that LxA4 and RvE1, neuroinflammatory resolution factor, were reduced in CM derived from nerve cells treated with SphK1 siRNA (FIG. 2c).

Figure 2D:
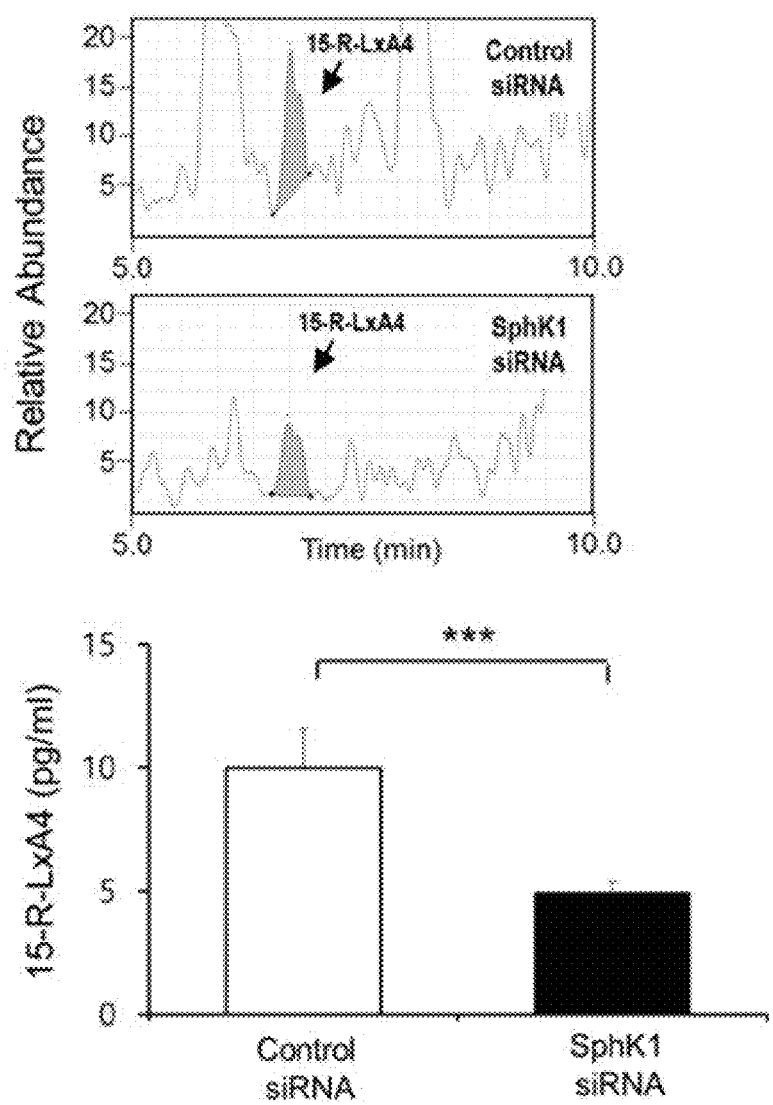

In addition, when the neuroinflammatory resolution factor were measured using LC-MS/MS, 15-R-LxA4 produced by COX2 acetylation was reduced in the nerve cells treated with SphK1 siRNA (FIG. 2d). That is, when SphK1 was inhibited, it could be confirmed that the neuroinflammatory resolution factor (especially, 15-R-LxA4) was reduced due to the reduction in COX2 acetylation.

3. In an Alzheimer's Animal Model, COX2 Acetylation and the Secretion of Neuroinflammatory Resolution Factor have been Reduced, which was Improved by SphK1 Overexpression.

Figure 3A:
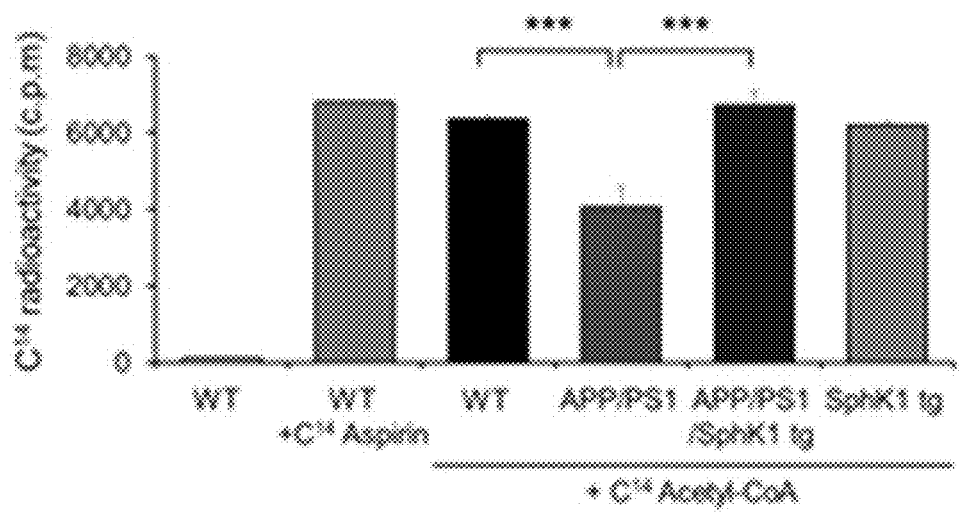
FIGS. 3a to 3c illustrate results of confirming that in APP/PS1 mice, acetylation of COX2 and secretion of neuroinflammatory resolution factor (SPMs) have been reduced and this reduction has been improved by overexpression of SphK1.

The present inventors treated [$^{14}$C] acetyl-CoA to nerve cells isolated from 9-month-old mice and analyzed the level of acetylation by purifying COX2 in order to confirm whether the results shown after treatment of SphK1 siRNA also occurred in an Alzheimer's animal model. Compared with wild-type mice, a low level of COX2 acetylation was shown in the nerve cells of APP/PS1 mice, and the acetylation of COX2 was increased in the nerve cells of APP/PS1/SphK1 tg mice (FIG. 3a).

Figure 3B:
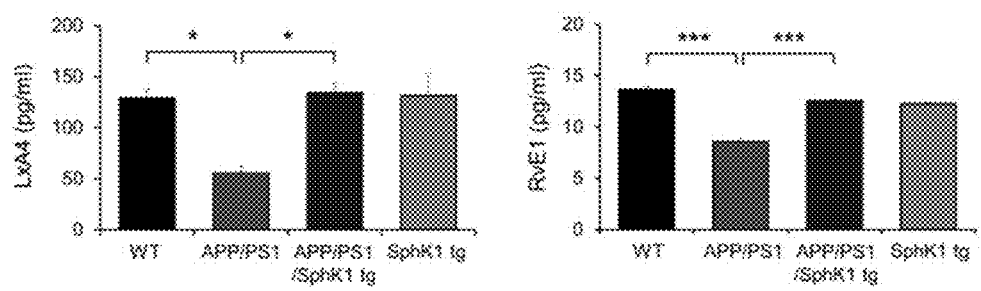
Figure 3C:
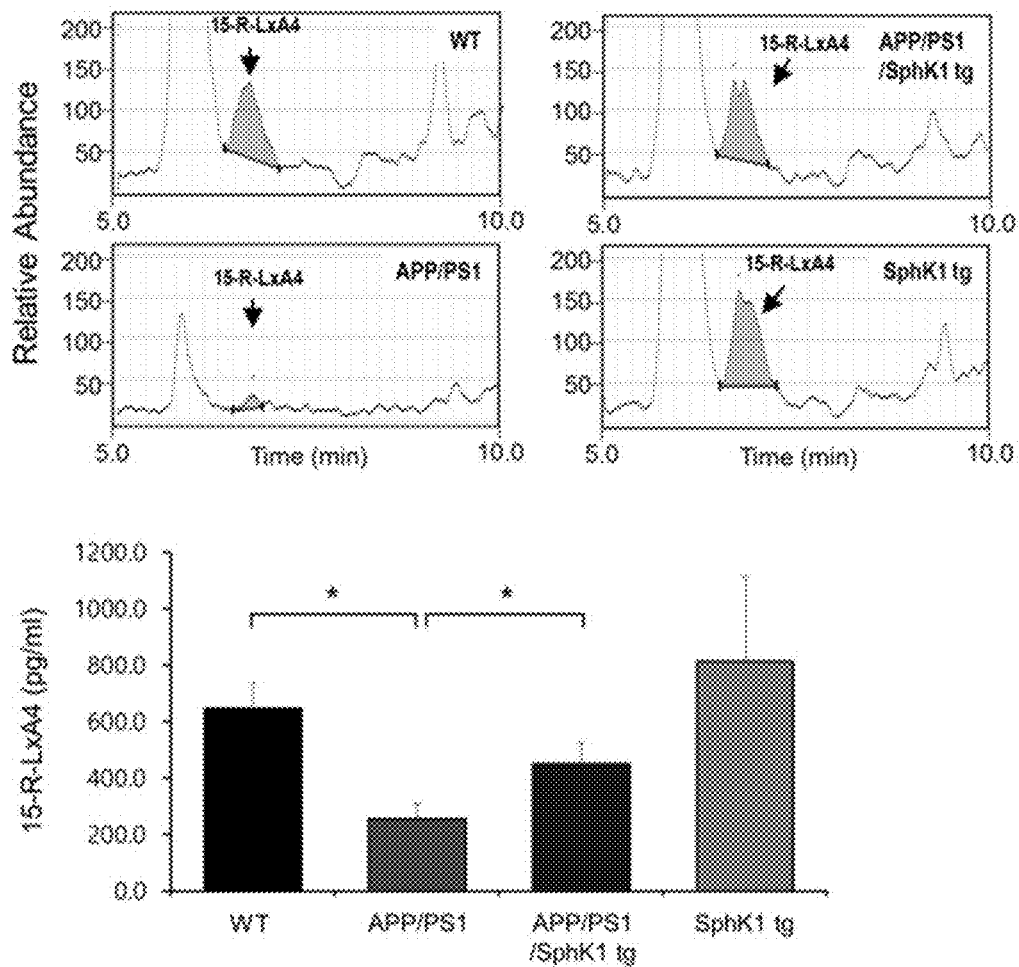

Expression levels of LxA4 and RvE1 were significantly decreased in CM derived from APP/PS1 nerve cells as compared to those in CM derived from wild-type nerve cells, and recovered in CM derived from APP/PS1/SphK1 tg cells (FIG. 3b). In addition, when the neuroinflammatory resolution factor were measured using LC-MS/MS, 15-R-LxA4 produced by COX2 acetylation was reduced in the Alzheimer's animal model and recovered when SphK1 was overexpressed (FIG. 3c). That is, the COX2 acetylation and the secretion of neuroinflammatory resolution factor were reduced in the Alzheimer's animal model, and it is meant that the reduction can be improved by overexpression of SphK1.

4. Increased SphK1 Regulates Neuroinflammation by Secreting Neuroinflammatory Resolution Factor in APP/PS1 Mice.

Figure 4A:
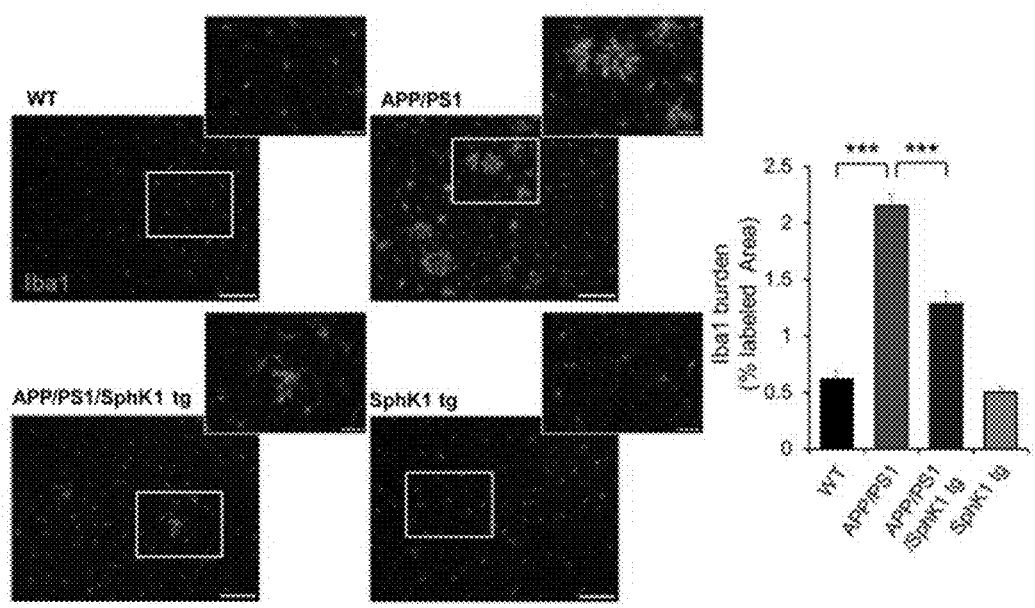
FIGS. 4a to 4c are results of confirming that neuroinflammatory resolution factor secreted by increased SphK1 in APP/PS1 mice reduce neuroinflammation.
Figure 4B:
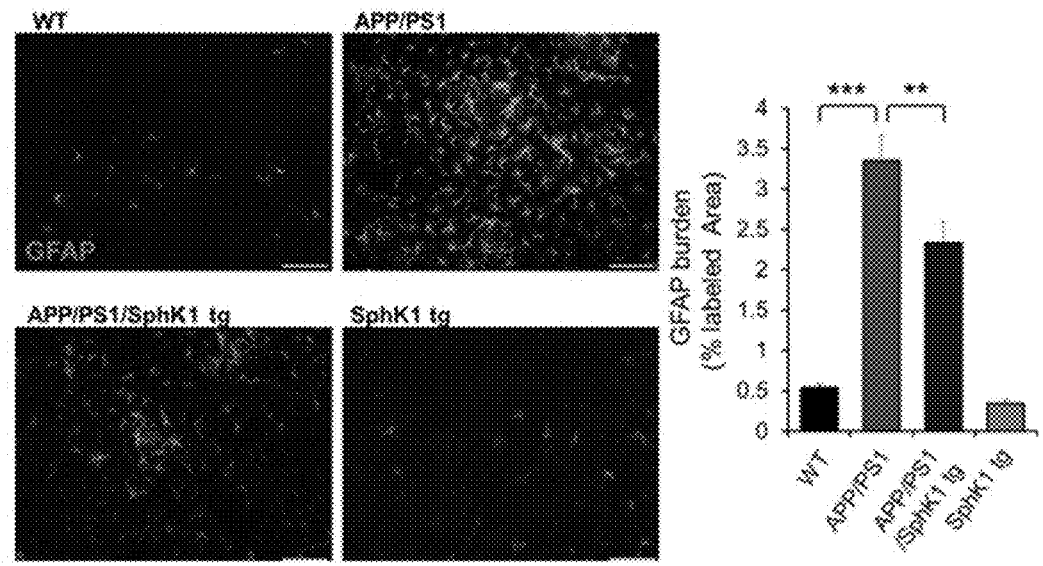
Figure 4C:
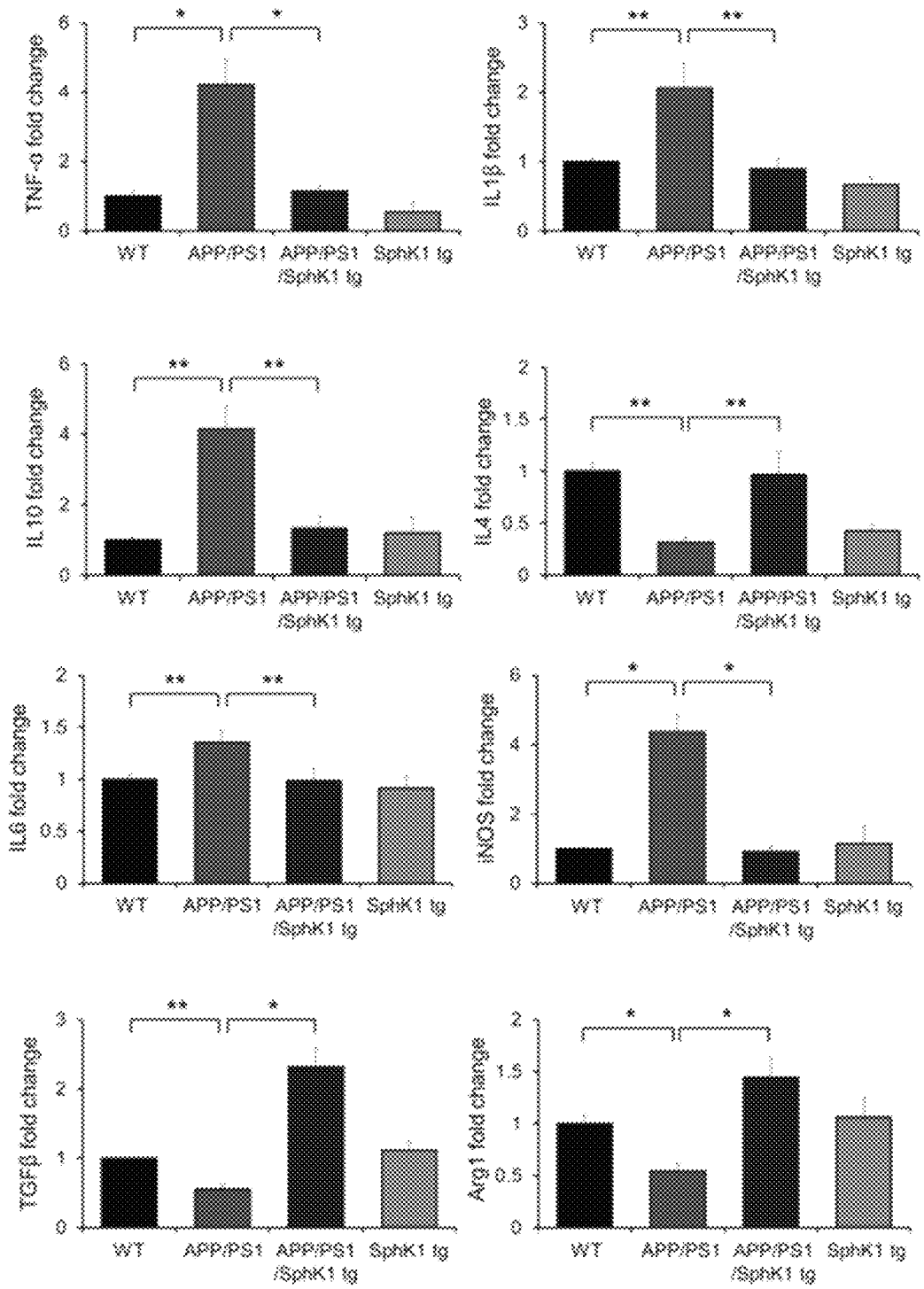

The present inventors observed changes in microglia and astrocytes in order to determine an effect of increased SphK1 on neuroinflammatory response by secreting neuroinflammatory resolution factor. The APP/PS1/SphK1 tg mice showed a remarkable decrease in microglia and astrocytes compared to the APP/PS1 mice (FIGS. 4a and 4b). In addition, APP/PS1/SphK1 tg mice showed a decrease in pro-inflammatory M1 markers and immune regulatory cytokines compared to APP/PS1 mice, and the expression of anti-inflammatory M2 markers was increased (FIG. 4c).

Collectively, these results indicate that SphK1 overexpression can improve the inflammatory response in the AD brain by promoting the secretion of neuroinflammatory resolution factor by inducing the acetylation of COX2.

5. Neuroinflammatory Resolution Factor Secreted by SphK1 Overexpression Regulate Aβ Phagocytosis of Microglia.

Figure 5A:
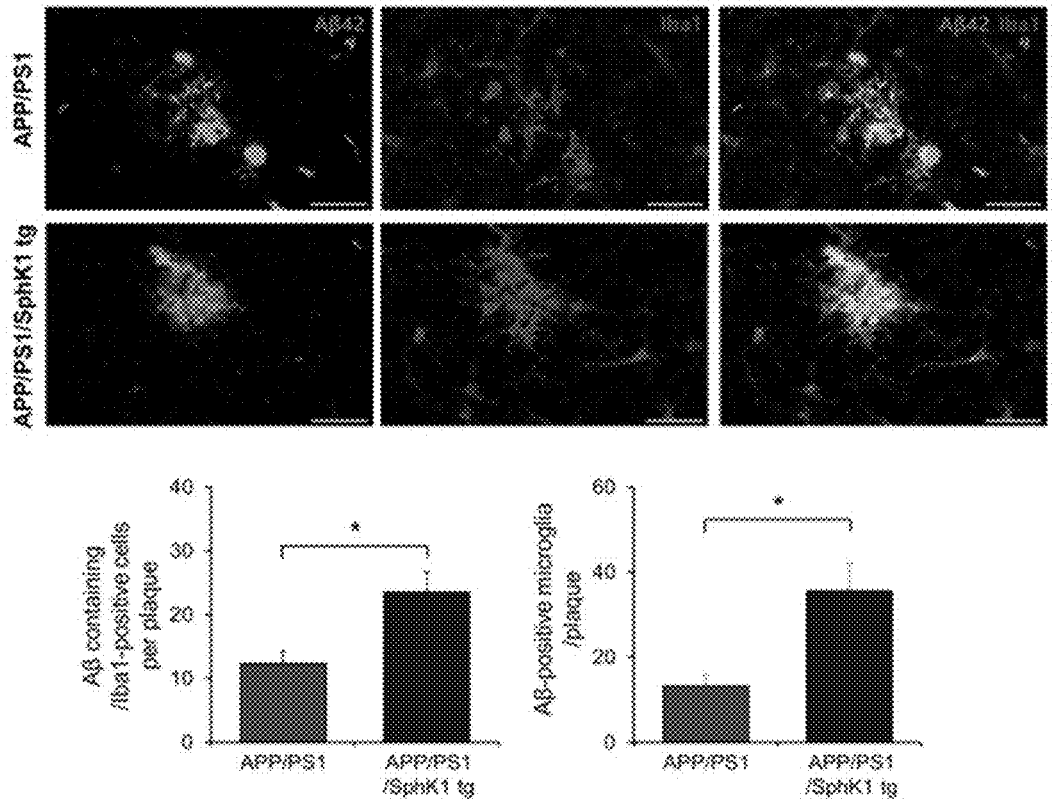
FIGS. 5a to 5f illustrate results of confirming that neuroinflammatory resolution factor secreted by increased SphK1 improve the phagocytosis of microglia.

To determine whether the neuroinflammatory resolution factor secreted by increased SphK1 recover the recruitment of microglia with Aβ, the number of microglia around plaques was quantified. As a result, the recruitment of microglia was increased in APP/PS1/SphK1 tg mice compared to APP/PS1 mice (FIG. 5a).

Figure 5B:
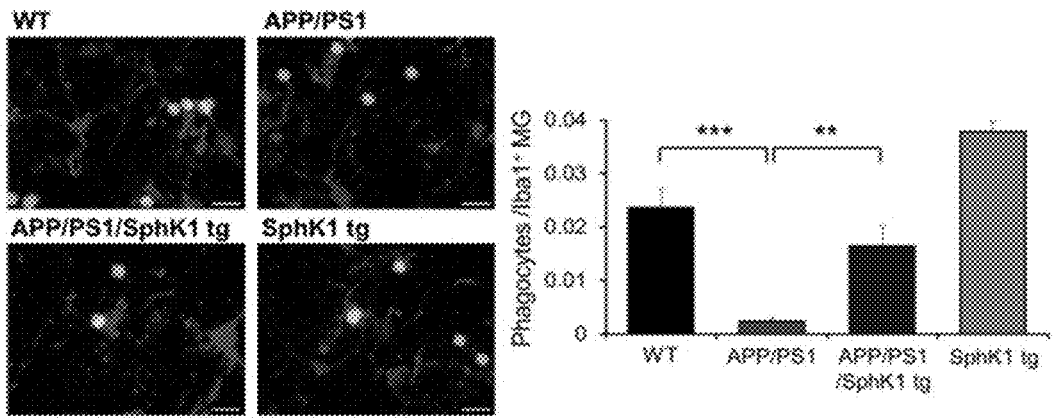
Figure 5C:
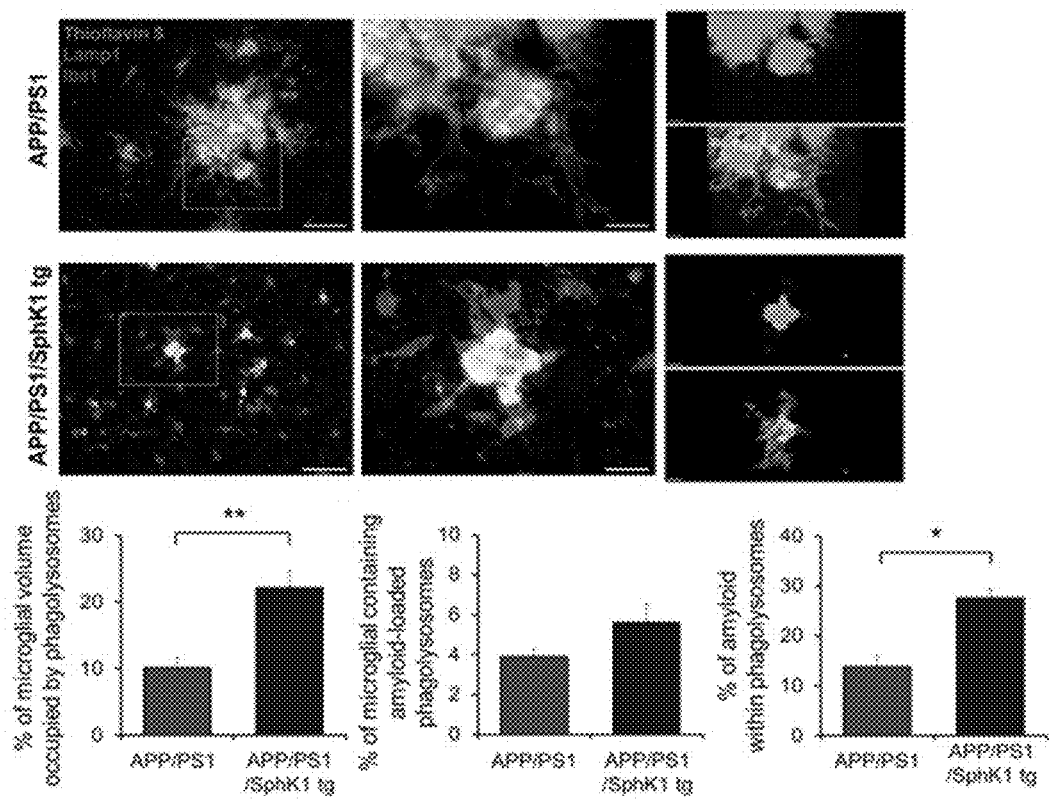

Next, a phagocytosis assay was performed using brain pieces. Compared to APP/PS1 mice, the number of microglia exhibiting phagocytosis was increased in APP/PS1/SphK1 tg mice (FIG. 5b). To further determine this effect, the Aβ phagocytosis of microglia was evaluated in vivo. The APP/PS1/SphK1 tg brain had an increased number of microglia stained with lysosomes and Aβ. Importantly, phagolysosomes in microglia were increased in the cortex of APP/PS1/SphK1 tg mice compared to APP/PS1 mice. As a result of analyzing plaque-related microglia, it was found that a ratio of cells containing Aβ incorporated in the phagolysosomes was increased in APP/PS1 mice overexpressing SphK1. The amount of Aβ contained in the phagolysosomes was increased in the brain of APP/PS1/SphK1 tg mice (FIG. 5c).

Figure 5D:
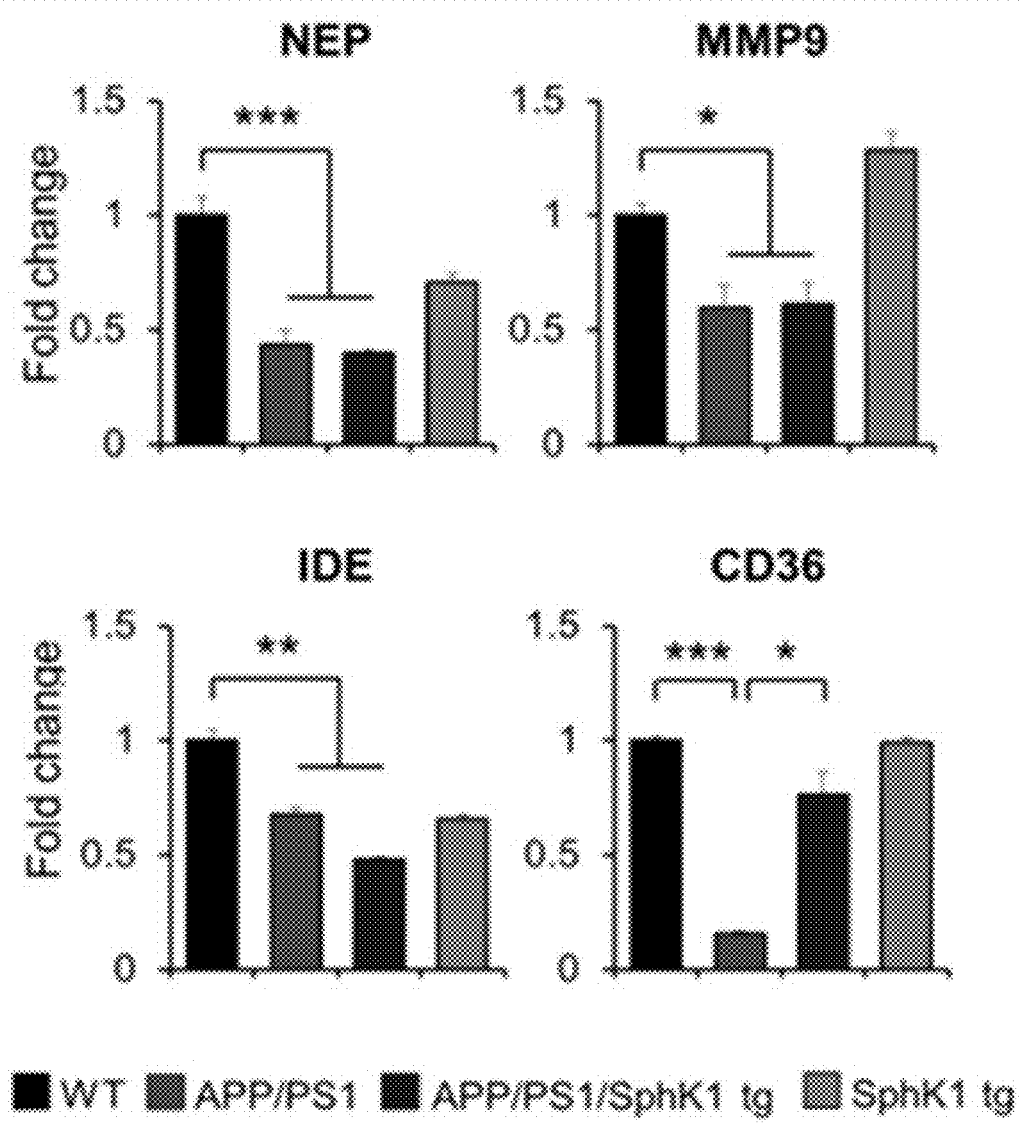
Figure 5E:
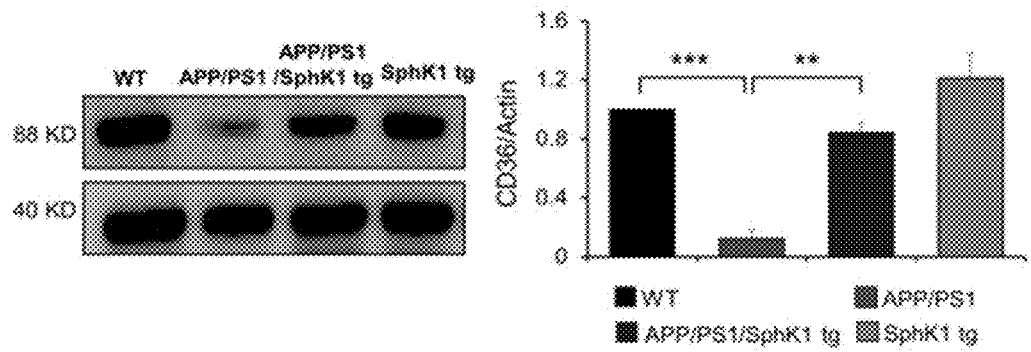

Next, the expression of Aβ degrading enzymes such as neprilysin (NEP), matrix metallopeptidase 9 (MMP9), and insulin degrading enzyme (IDE) was analyzed. Although the expression levels of these enzymes were not changed, CD36, which was known to increase when the phagocytosis of microglia occurred, was recovered in APP/PS1/SphK1 tg mice (FIGS. 5d and 5e).

Figure 5F:
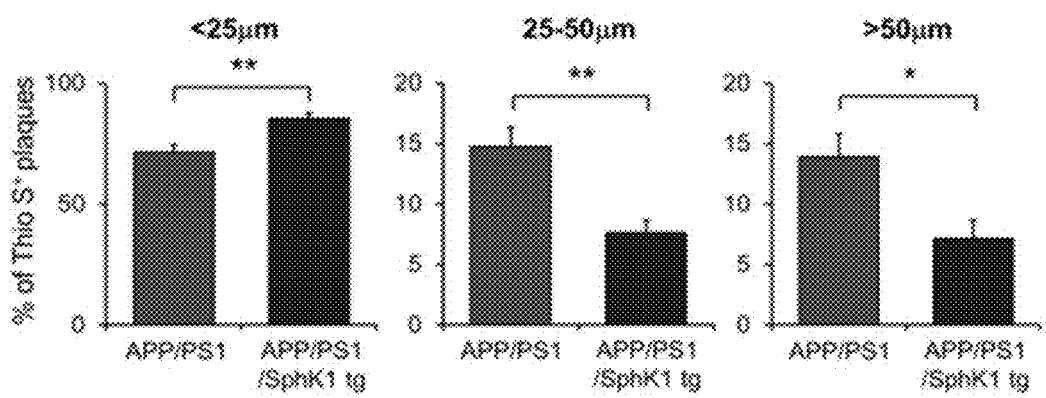

On the other hand, it is known that the phagocytosis of microglia induces a decrease in an outer part of Aβ compared to a core of the Aβ plaque. In the analysis of the morphology of Aβ plaques, in APP/PS1/SphK1 tg mice, it was confirmed that small (<25 μm) plaques were significantly increased, and medium (25 to 50 μm) and large (>50 μm) plaques were significantly decreased, and thus, the outer part was phagocytosed by microglia (FIG. 5f).

Through the above results, it was found that the increased SphK1 of the nerve cells increased the acetylation of COX2 to increase the secretion of the neuroinflammatory resolution factor, and as a result, it could be seen that the Aβ phagocytosis of microglia has increased in APP/PS1 mice.

6. Neuroinflammatory Resolution Factor Secreted by SphK1 Overexpression Alleviate AD Lesions in Mice.

Figure 6A:
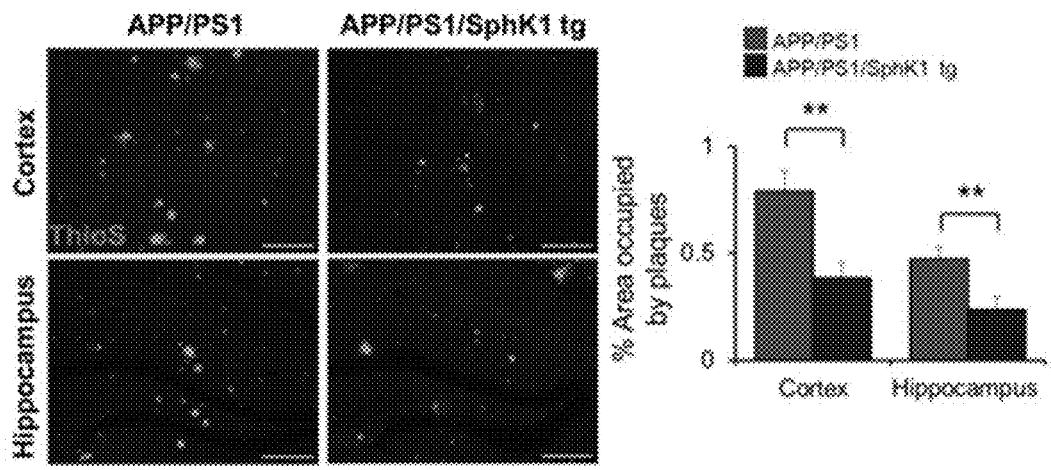
FIGS. 6a to 6i illustrate results of showing that neuroinflammatory resolution factor secreted by increased SphK1 in APP/PS1 mice reduce AD lesions.
Figure 6B:
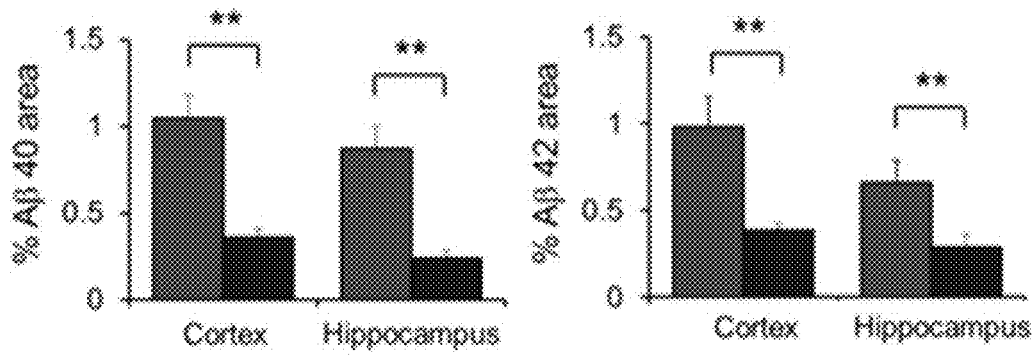
Figure 6C:
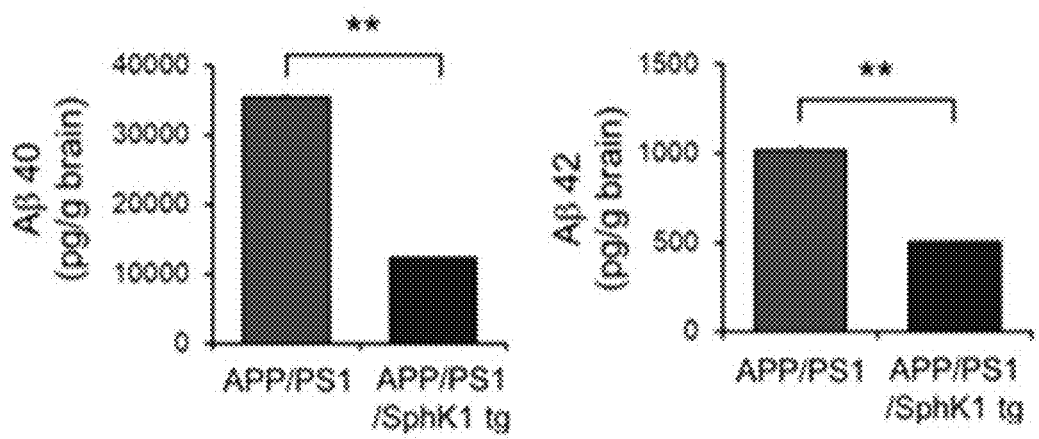
Figure 6D:
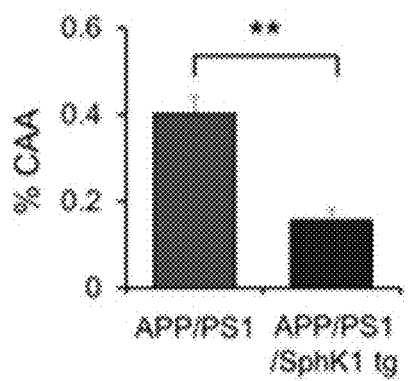
Figure 6E:
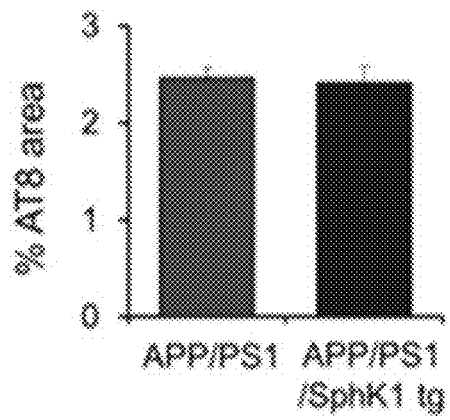
Figure 6F:
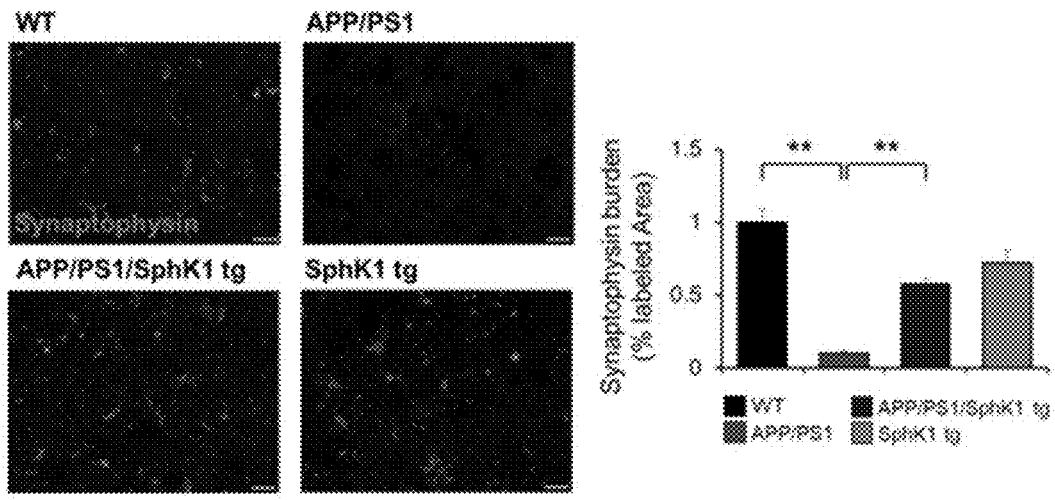
Figure 6G:
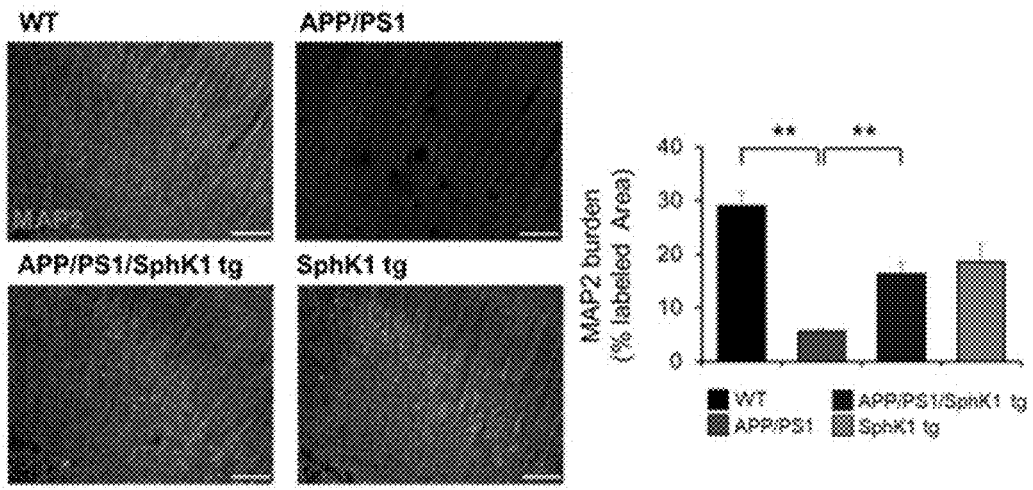
Figure 6H:
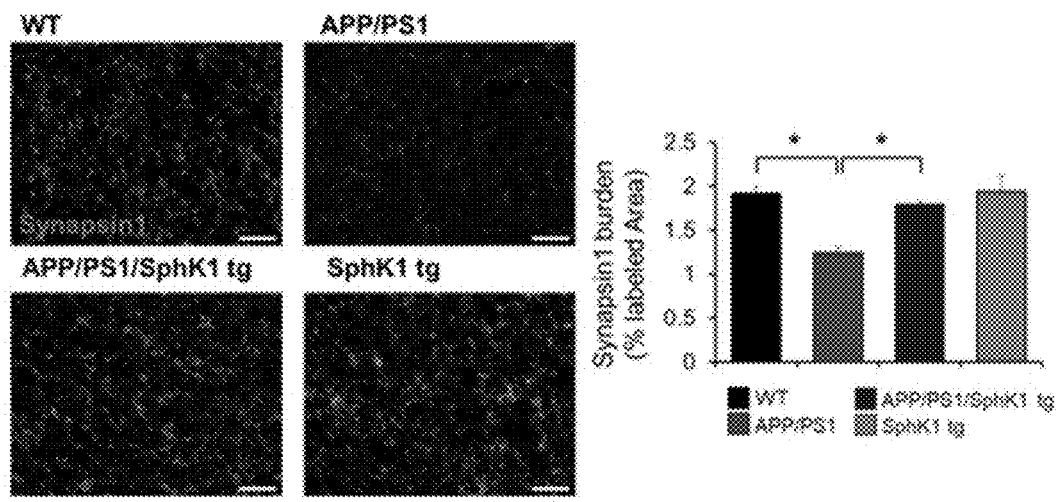
Figure 6I:
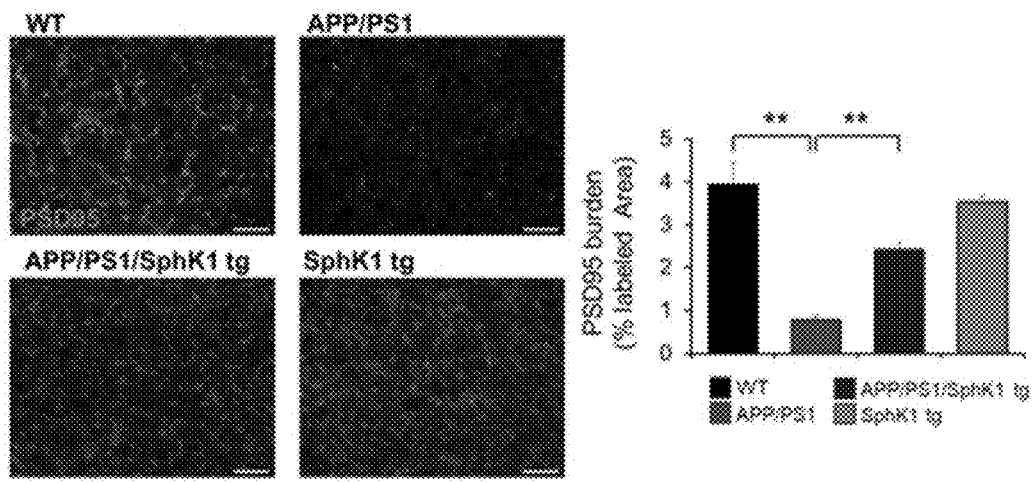

In order to find how the neuroinflammatory resolution factor secreted by the increased SphK1 activity in APP/PS1/SphK1 tg mice had affected the lesions of AD, an Aβ profile was firstly identified. As experiment results of thioflavin S (ThioS) staining, immunofluorescence staining, and ELISA of A1340 and A1342, it was shown that Aβ was significantly lowered in APP/PS1/SphK1 tg mice compared to APP/PS1 mice (FIGS. 6a to 6c). In APP/PS1/SphK1 tg mice, amyloid angiopathy of the brain was also reduced (FIG. 6d). Compared to wild-type mice, label densities of synaptophysin, MAP2, synapsin1 and PSD95 were reduced in APP/PS1 mice. However, in APP/PS1/SphK1 tg mice, the label densities were recovered to levels similar to those of the wild-type mice (FIGS. 6f to 6i).

7. Neuroinflammatory Resolution Factor Secreted by SphK1 Overexpression Recover Cognitive Function in an Alzheimer's Animal Model.

The present inventors also performed a Morris Water Maze test and a fear conditioning test to evaluate changes in learning and memory. It was confirmed that the old APP/PS1 mice exhibited serious problems in memory formation, while the APP/PS1/SphK1 tg mice alleviated these problems to some extent (FIGS. 7a to 7f).

Figure 7A:
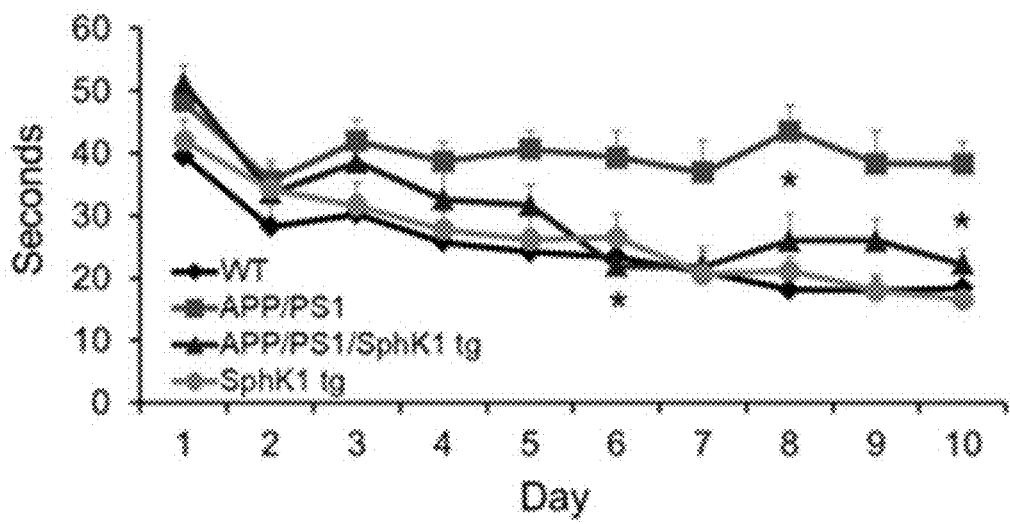
FIGS. 7a to 7h are diagrams illustrating that an increase in neuroinflammatory resolution factor secreted by SphK1 overexpression in APP/PS1 mice has recovered a cognitive function.
Figure 7B:
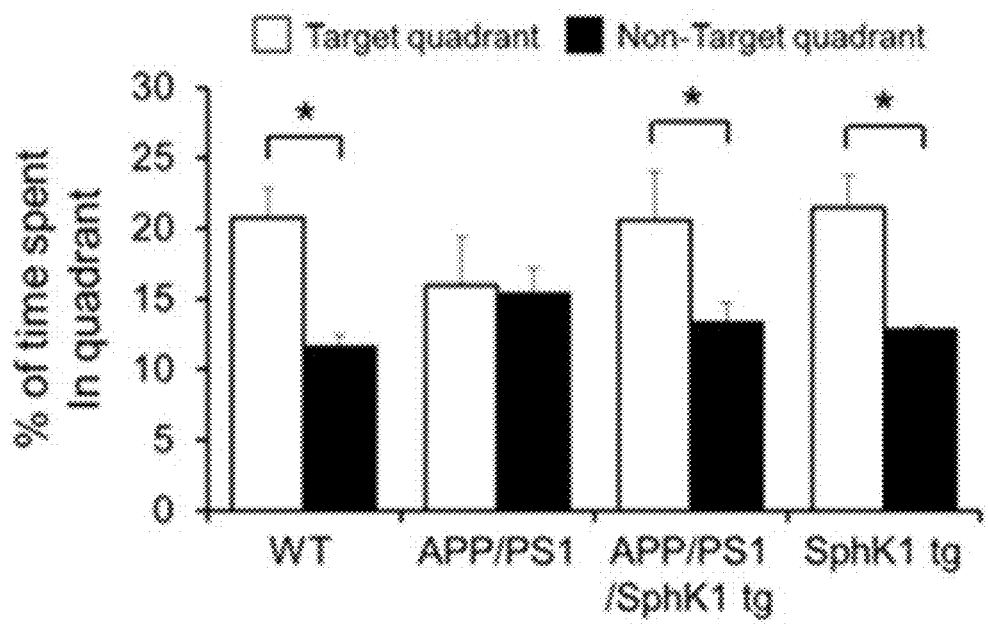
Figure 7C:
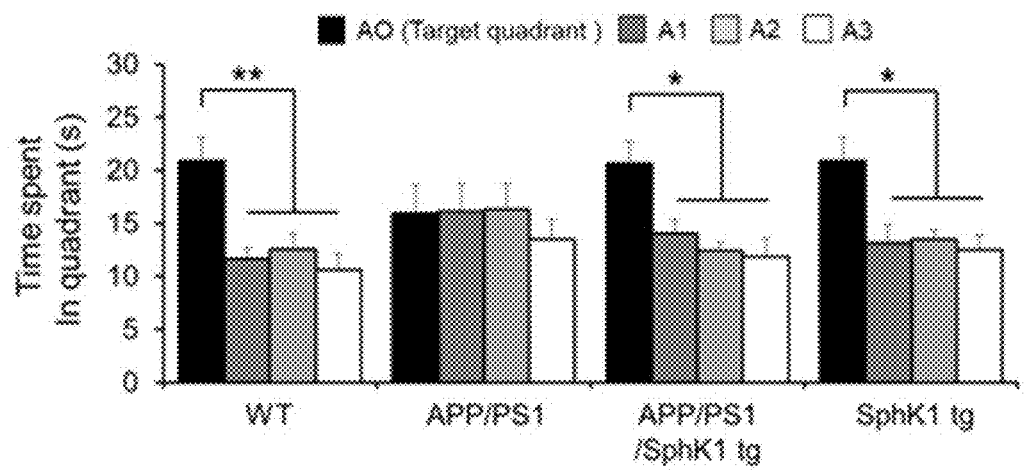
Figure 7D:
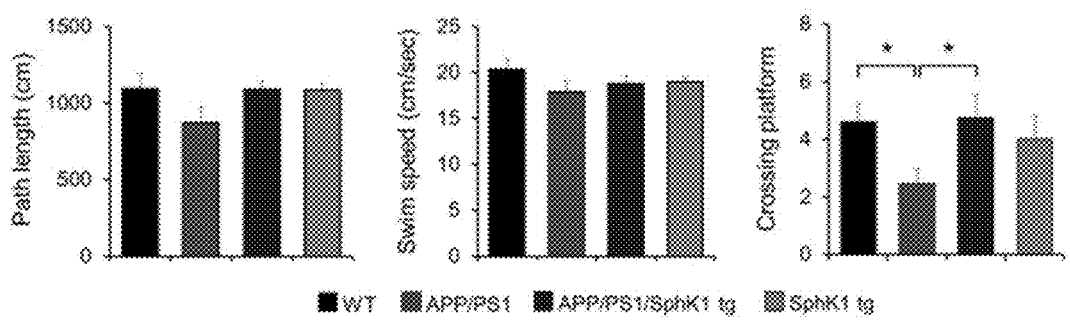
Figure 7E:
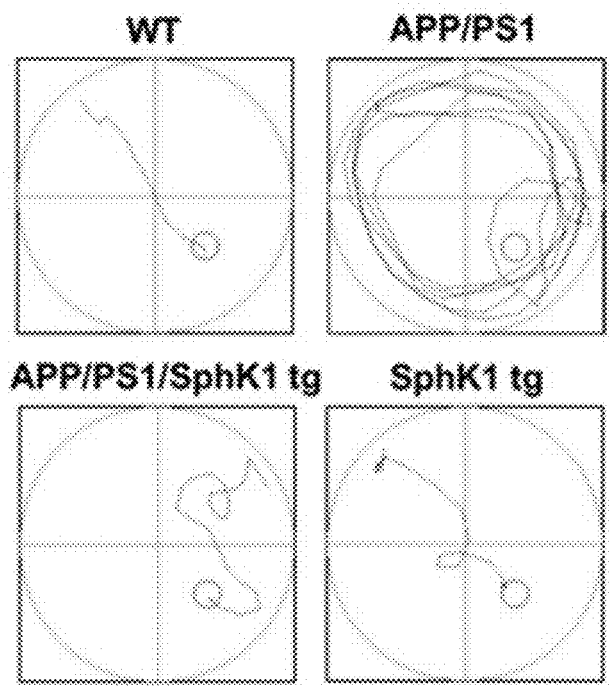
Figure 7F:
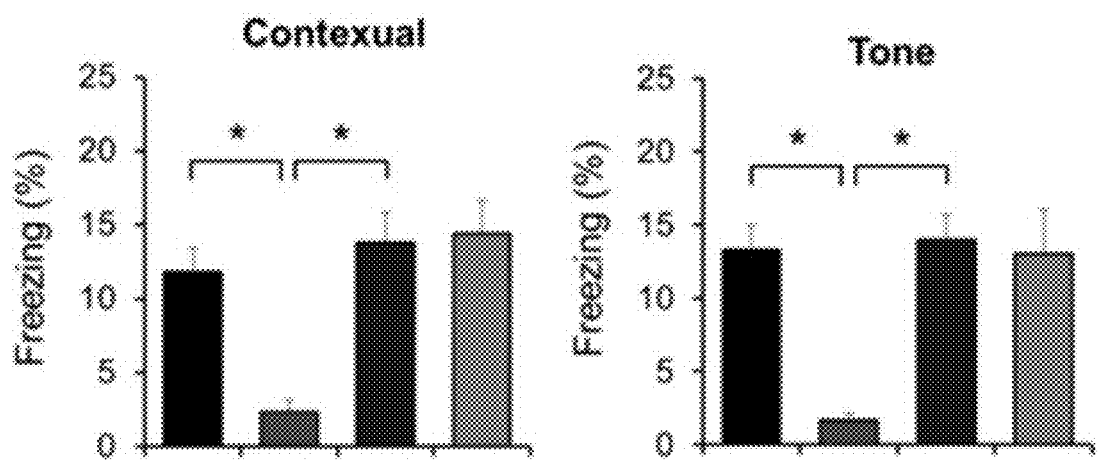
Figure 7G:
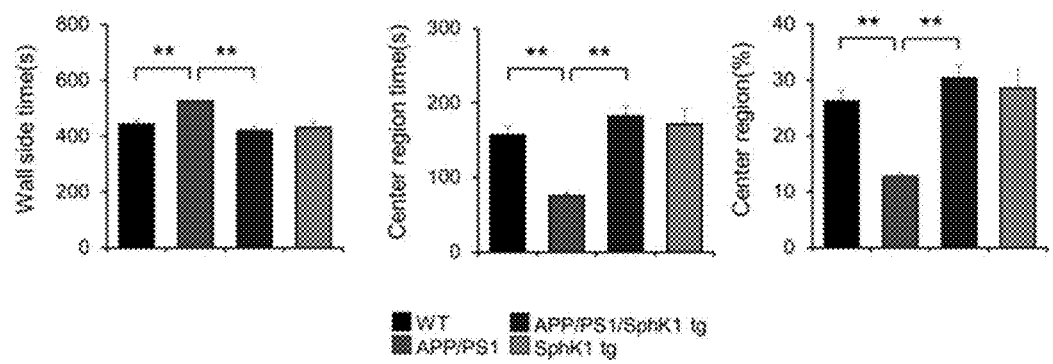
Figure 7H:
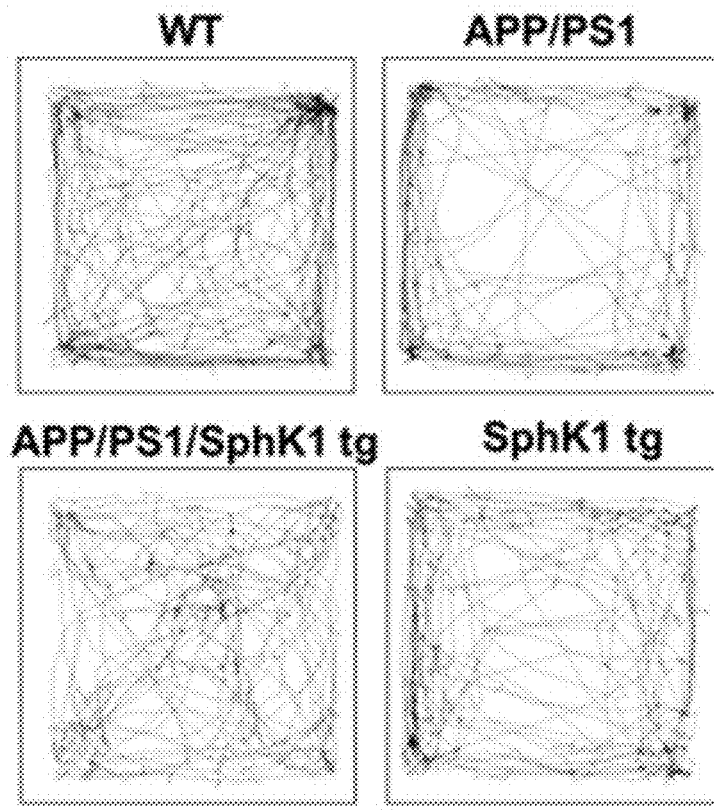

An open field test was performed to evaluate motor ability and immediate activity. The APP/PS1/SphK1 tg mice showed improved motor ability and immediate activity compared to the APP/PS1 mice (FIGS. 7g to 7h).

Overall, these results indicate that compared to APP/PS1 mice, in APP/PS1/SphK1 tg mice, the expression of SphK1 is increased in nerve cells, resulting in increased acetylation of COX2, and as a result, the accumulation of Aβ has been reduced and learning and learning have been improved.

8. A COX2 Acetylating Agent Produced by SphK1 Promotes the Secretion of Neuroinflammatory Resolution Factor.

Based on the experimental results, the present inventors conducted a series of experiments to directly confirm whether a compound capable of inducing the acetylation of COX2 exhibits an effect of preventing or treating degenerative neurological diseases.

Figure 8A:
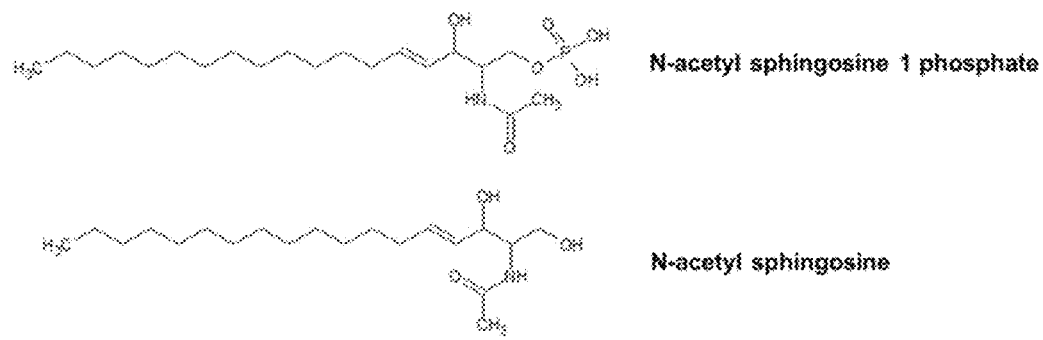
FIGS. 8a to 8d are diagrams illustrating that a COX2 acetylating agent produced by SphK1 promotes the secretion of neuroinflammatory resolution factor.

Specifically, the present inventors predicted that N-acetyl sphingosine 1 phsosphate and N-acetyl sphingosine could induce the acetylation of COX2, and the following experiments were conducted using this (FIG. 8a).

Figure 8B:
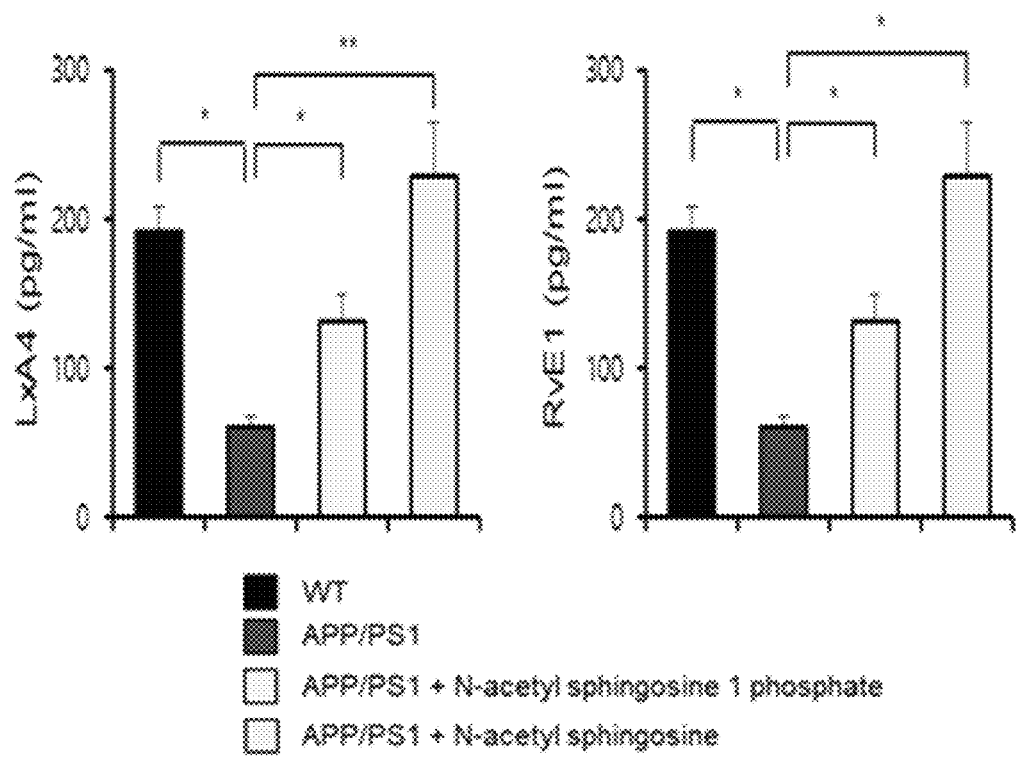

First, in order to confirm whether the selected compounds promote the secretion of neuroinflammatory resolution factor in nerve cells, APP/PS1 nerve cells were treated with N-acetyl sphingosine 1 phsosphate or N-acetyl sphingosine, and then the expression levels of the neuroinflammatory resolution factor were confirmed. As a result, it was confirmed that the expression levels of LxA4 and RvE1 in nerve cells of APP/PS1 mice were recovered when treated with N-acetyl sphingosine 1 phsosphate or N-acetyl sphingosine (FIG. 8b).

Figure 8C:
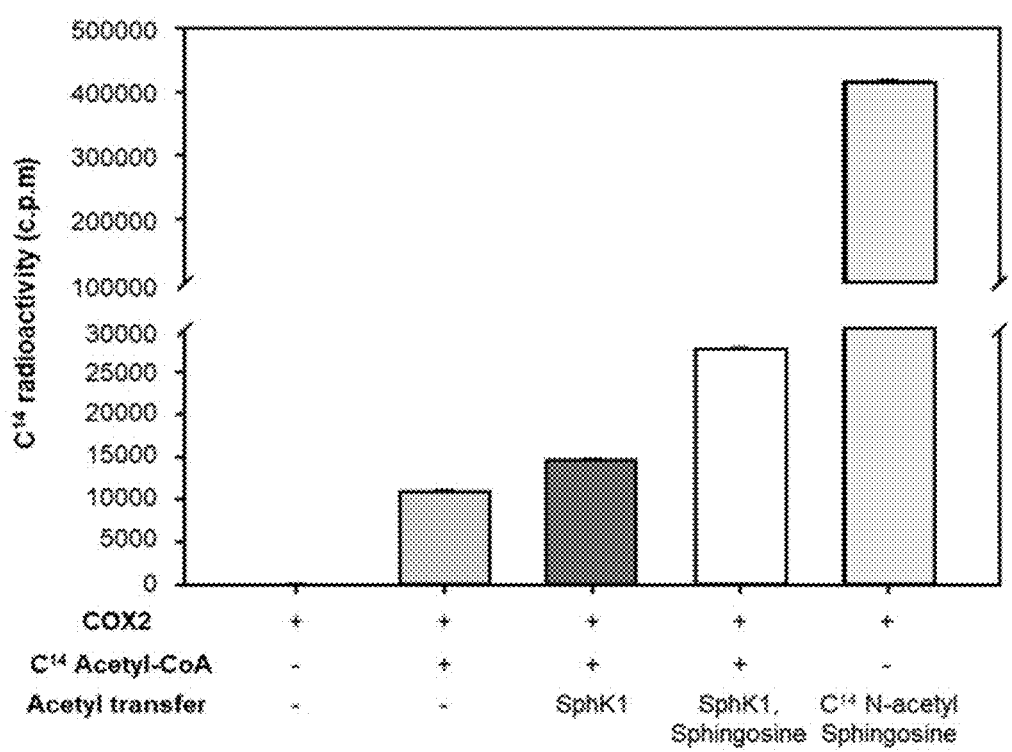
Figure 8D:
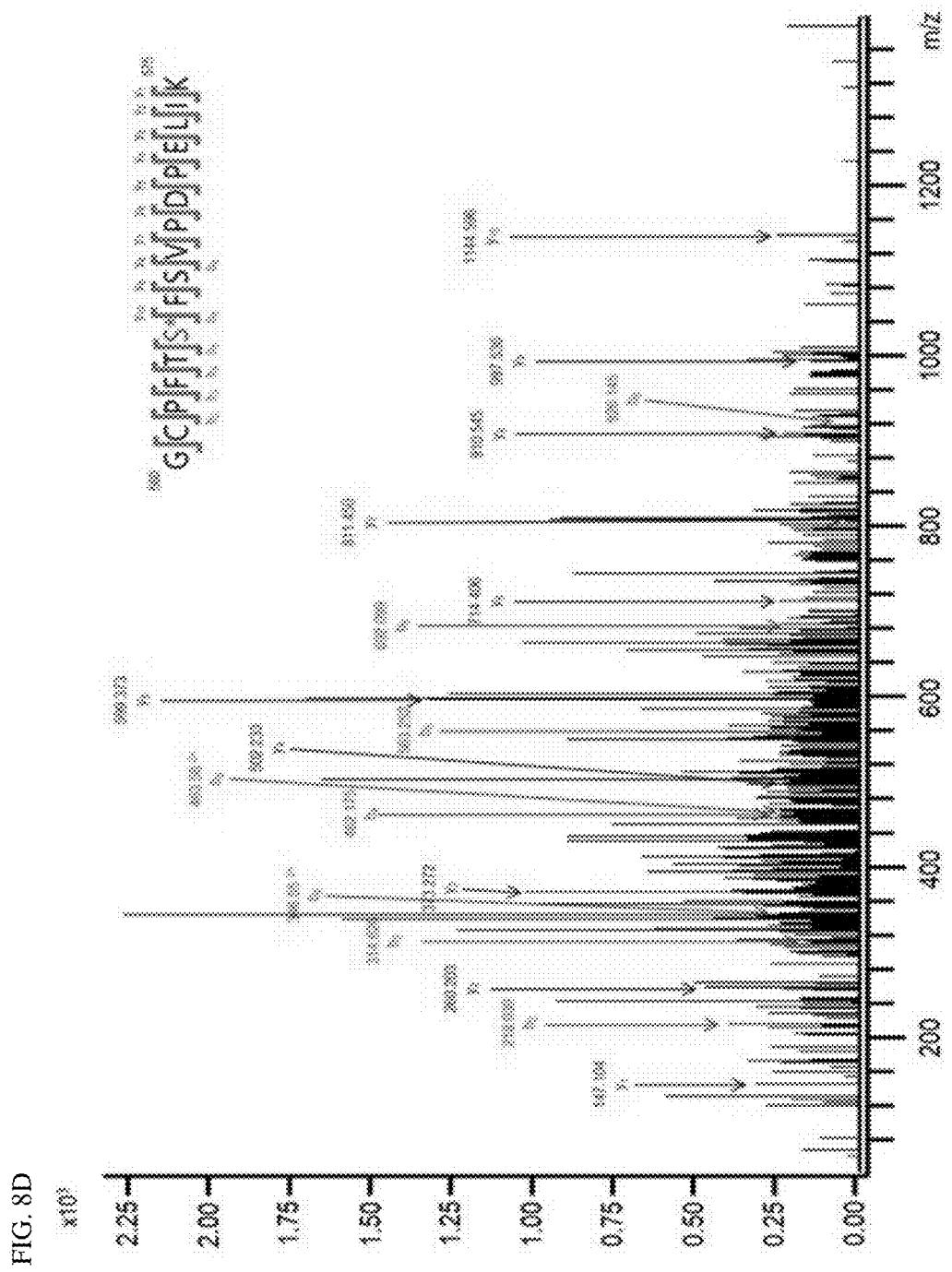

Next, in order to confirm whether the secretion of the neuroinflammatory resolution factor was caused by the increase in acetylation of COX2, it was confirmed by using N-acetyl sphingosine labeled to $C^{14}$, and it was confirmed that $C^{14}$ N-acetyl sphingosine caused more acetylation than a sample mixed with SphK1, acetyl-CoA, and sphingosine confirmed above (FIG. 8c). In addition, it was confirmed that serine 565 (S565) for a peptide 560-GCPFTSFSVPDPE-LIK-575 of COX2 was acetylated in the presence of N-acetyl sphingosine (FIG. 8d).

That is, it was confirmed that the compounds induced the COX2 acetylation to promote the secretion of the neuroinflammatory resolution factor, and in particular, by directly confirming that this acetylation occurred at S565 of COX2, in the treatment of degenerative neurological diseases, it was confirmed once again that S565 acetylation of COX2 may be a very critical therapeutic target.

9. The COX2 Acetylating Agent Reduces AD Lesions in an Alzheimer's Animal Model by Promoting the Secretion of Neuroinflammatory Resolution Factor.

Figure 9A:
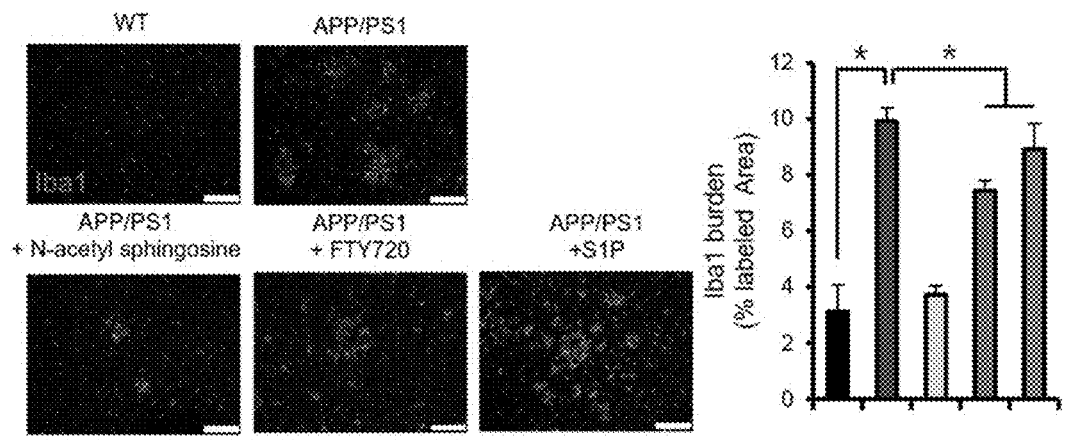
FIGS. 9a to 9d are diagrams illustrating that a COX2 acetylating agent promotes secretion of neuroinflammatory resolution factor to reduce AD lesions of an Alzheimer's animal models.
Figure 9B:
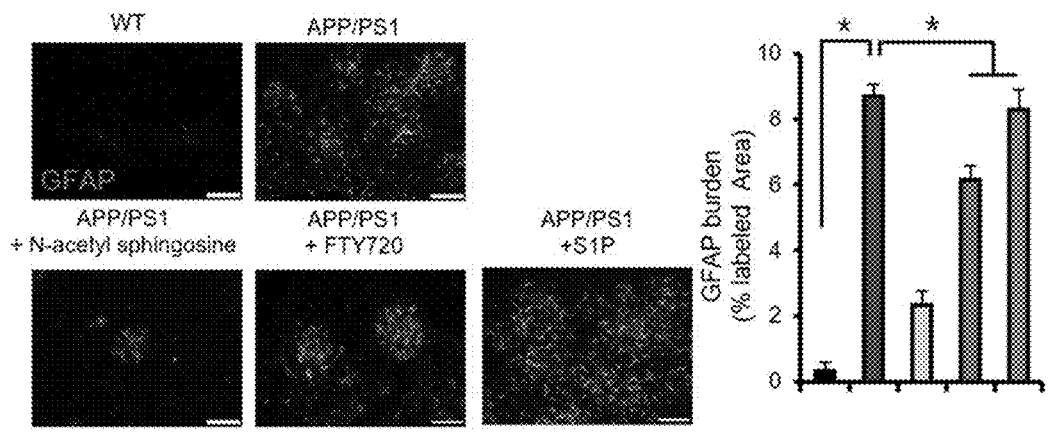
Figure 9C:
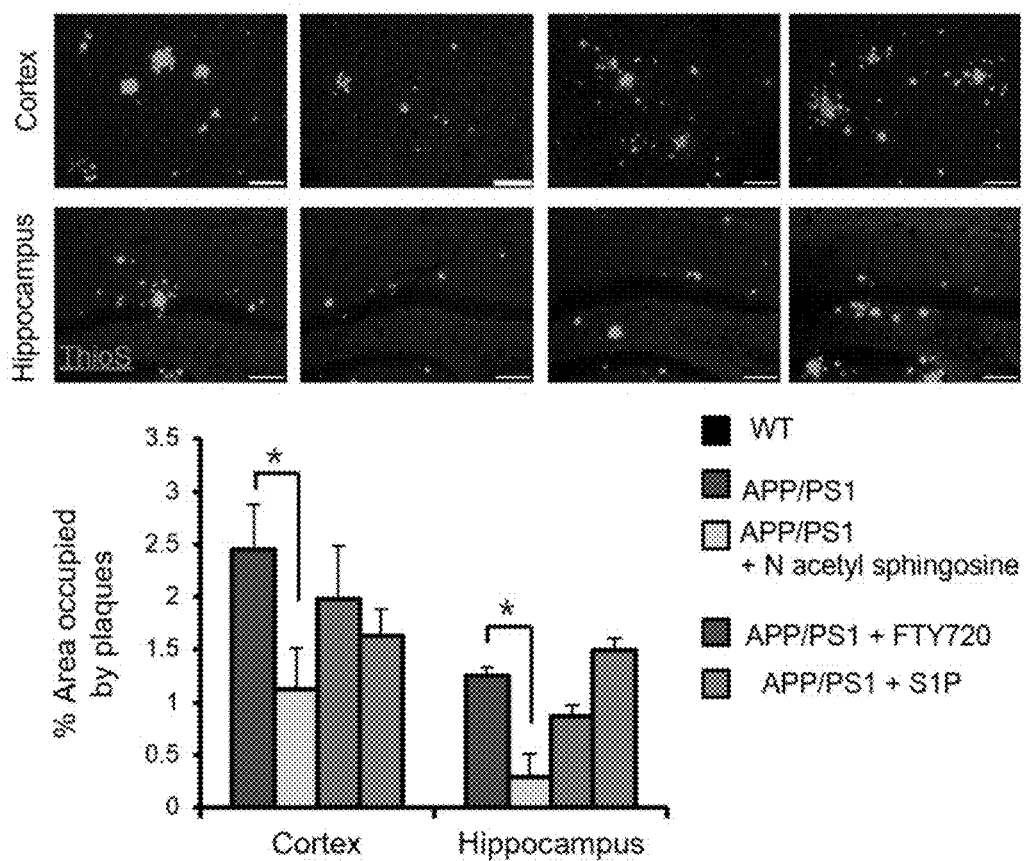
Figure 9D:
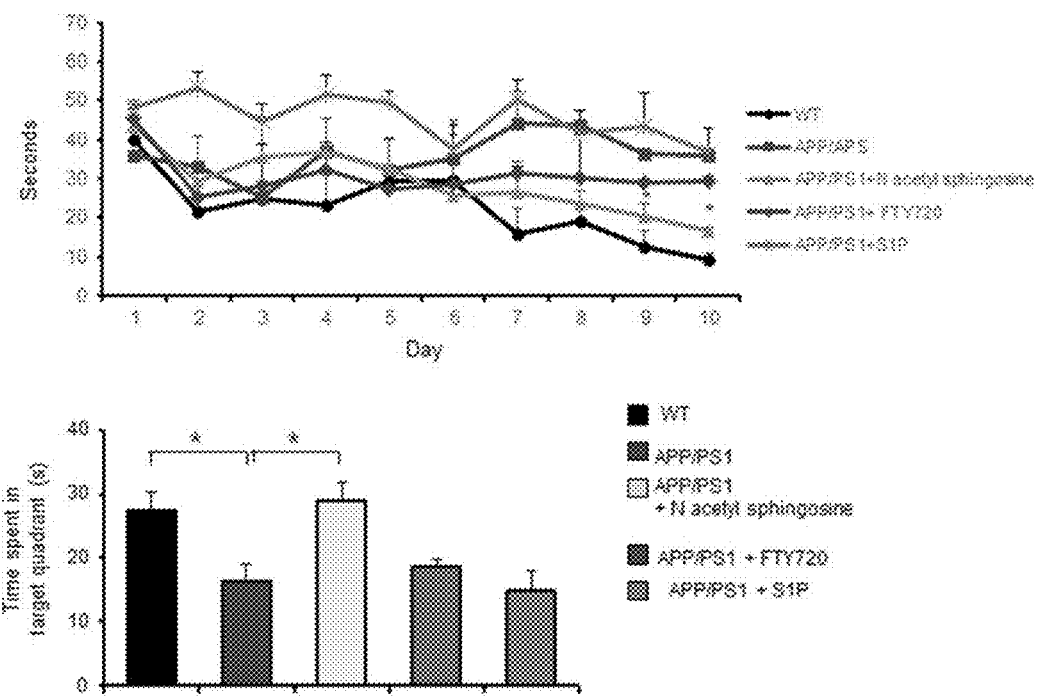

The present inventors confirmed AD lesions by injecting N-acetyl sphingosine, one of COX2 acetylating agents identified through the above experiment, into an APP/PS1 animal model. First, in order to determine an effect of N-acetyl sphingosine on neuroinflammatory response by secreting the neuroinflammatory resolution factor, changes in microglia and astrocytes were observed. The APP/PS1 mice injected with N-acetyl sphingosine showed a remarkable decrease in microglia and astrocytes compared to the APP/PS1 mice (FIGS. 9a and 9b). In addition, it was found that the amount of Aβ was significantly lowered in APP/PS1 mice injected with N-acetyl sphingosine compared to APP/PS1 mice, and it was confirmed that memory and cognition were improved (FIGS. 9c and 9d). However, when sphingosine derivatives FTY720 and S1P were injected, there was no difference in the activity of microglia and astrocytes compared to the Alzheimer's animal model, and there was no effect of reducing Aβ deposition and improving memory (FIGS. 9a and 9b).

Through the above results, it was confirmed that unlike sphingosine derivatives such as FTY720 and S1P, the COX2 acetylating agent promoted the secretion of neuroinflammatory resolution factor to exhibit an effect of reducing AD lesions, such as reduction in neuroinflammation, a decrease in Aβ deposition, and improvement in memory in APP/PS1 mice.

10. Preparation and Efficacy Verification of Antibody (ac-S565) that Specifically Recognizes Acetylated S565 Residue in COX2 Protein Based on the results of the above Examples, the present inventors have prepared an antibody that specifically recognized S565 acetylated in a COX2 protein represented by SEQ ID NO: 1 and intended to use the antibody in the following experiments.

Specifically, after preparing a peptide of SEQ ID NO: 2, a rabbit was immunized by injecting the peptide, and then a polyclonal antibody (hereinafter referred to as "ac-S565 antibody") was isolated and purified from the rabbit serum.

Meanwhile, referring to the above experimental results, the COX2 protein was acetylated at a residue S516 by aspirin, and was not acetylated at S565. However, the acetylation occurred specifically at the residue S565 of COX2 by N-acetyl sphigosine (N-AS).

Based on these results, the present inventors confirmed whether to acetylate S565 of COX2 by performing Western blotting using an ac-S565 antibody without treating an acetyl transfer to a recombinant COX2 protein, or after treating aspirin or N-AS.

Figure 10:
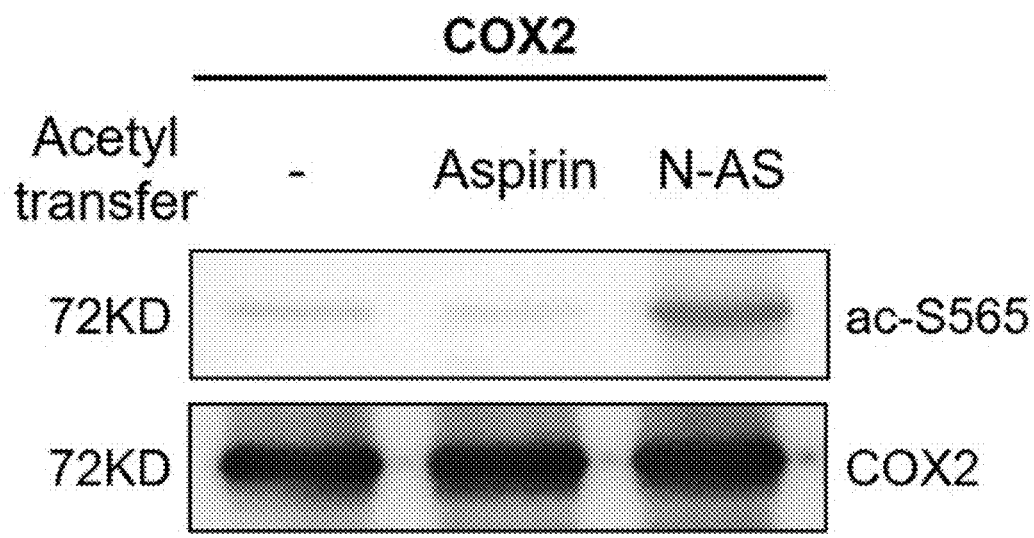
FIG. 10 illustrates a result of confirming that an ac-S565 antibody specifically detects the acetylation of a S565 residue of COX2 (N-AS: N-acetyl sphingosine).

As a result, it was confirmed that a band was hardly detected in the Western blot experiment using the ac-S565 antibody in the COX2 that was not treated with acetyl transfer or treated with aspirin, but the band was strongly shown in the COX2 treated with N-AS (FIG. 10). Through these results, it was confirmed that the prepared ac-S565 antibody could specifically detect whether to acetylate S565 of COX2, and furthermore, it was confirmed again that N-AS was a substance that acetylated S565 of COX2.

11. Confirmation of Reduction of Acetylation of S565 of COX2 in Brain Tissue of Alzheimer's Animal Model The present inventors confirmed the level of COX2 S565 acetylation in brain tissues of wild-type mice (WT) and an Alzheimer's animal model (APP/PS1) by using the prepared ac-S565 antibody through fluorescence immunostaining.

Figure 11:
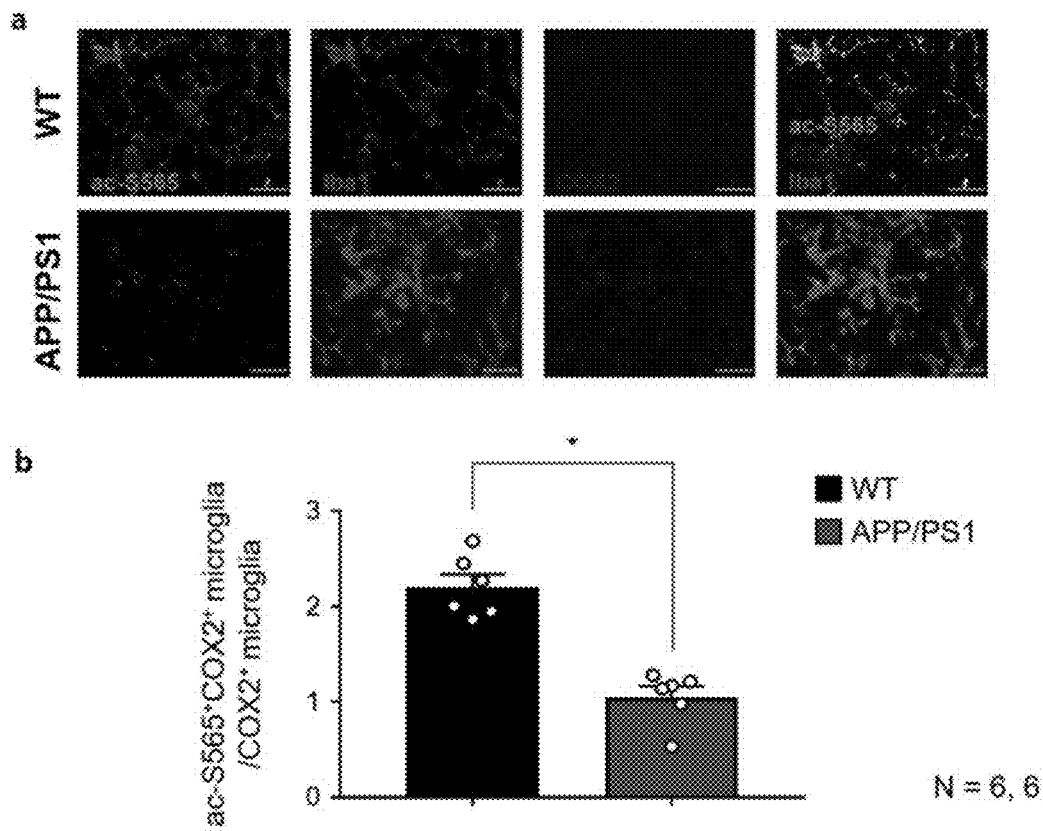
FIG. 11a illustrates a result of confirming the levels of acetylation of a COX2 protein and S565 of COX2 expressed in microglia derived from wild-type (WT) and APP/PS1 mice through fluorescence immunostaining.
FIG. 11b illustrates a result of quantifying the levels (n=6/group).

As a result, it was confirmed that the expression of COX2 was increased and the S565 acetylation of COX2 was decreased in microglia of the brain tissue of an Alzheimer's animal compared to wild-type mice. That is, these results indicate that the S565 acetylation of COX2 is reduced in microglia of the Alzheimer's animal model (FIGS. 11a and 11b).

The present inventors reconfirmed the level of COX2 S565 acetylation in microglia of the Alzheimer's animal model through Western blot.

Figure 12:
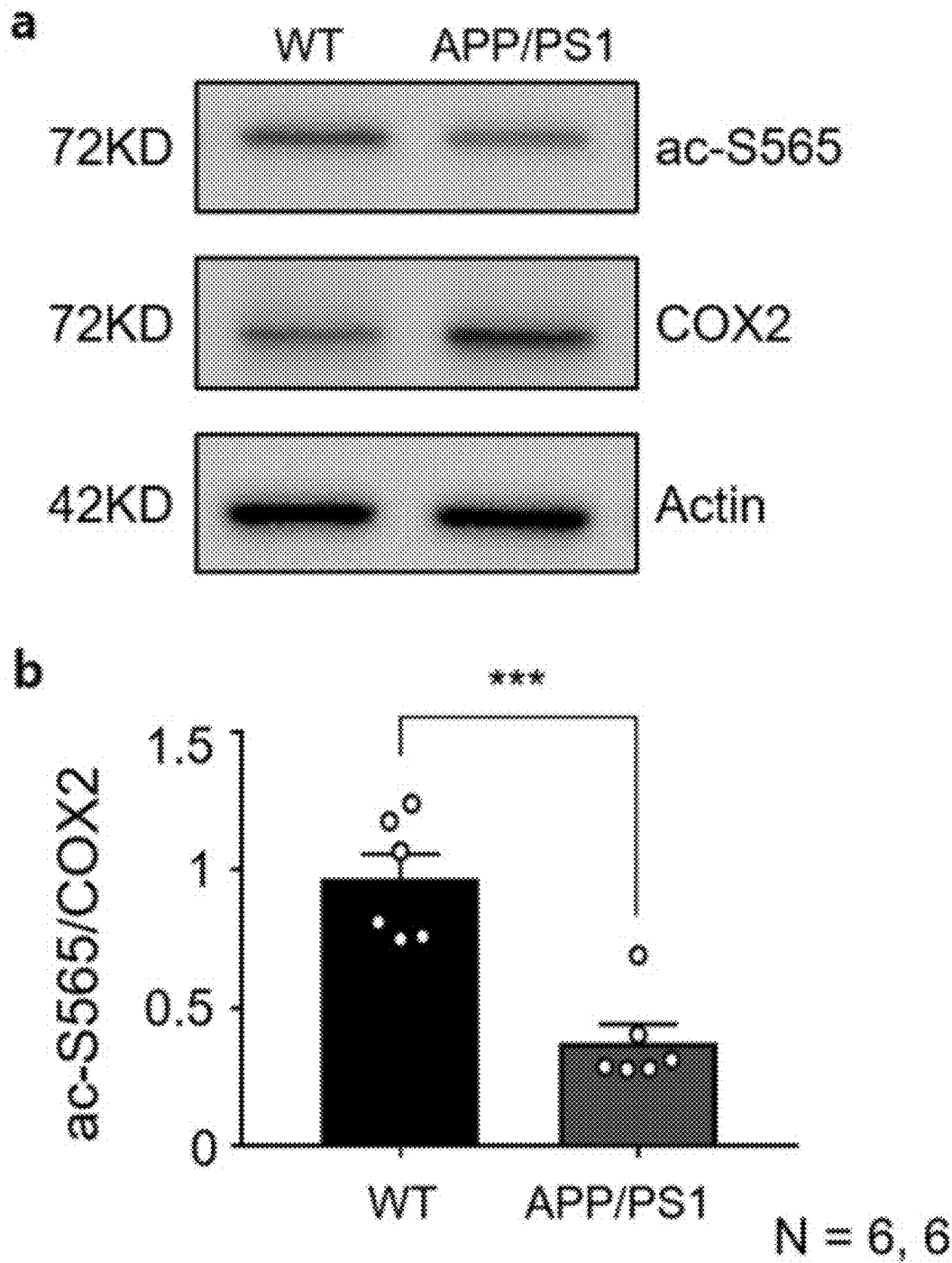
FIG. 12a illustrates a result of confirming the levels of acetylation of a COX2 protein and S565 of COX2 expressed in microglia derived from wild-type and APP/PS1 mice through Western blotting.
FIG. 12b illustrates a result of quantifying the levels (n=6/group).

As a result, like the fluorescence immunostaining result, it was confirmed that the expression of COX2 was increased and the S565 acetylation of COX2 was decreased in the microglia of the Alzheimer's animal compared to wild-type mice. That is, these results indicate that the S565 acetylation of COX2 is reduced in the microglia of the Alzheimer's animal model (FIGS. 12a and 12b).

Through this result, it can be confirmed that degenerative neurological diseases can be diagnosed by analyzing the level of S565 acetylation of COX2.

12. Confirmation of Reduction in S565 Acetylation of COX2 in Microglia Treated with Amyloid Beta The present inventors created a neuroinflammatory environment by treating human-derived microglia with amyloid beta, and then confirmed the level of S565 acetylation of COX2 through fluorescence immunostaining.

Figure 13:
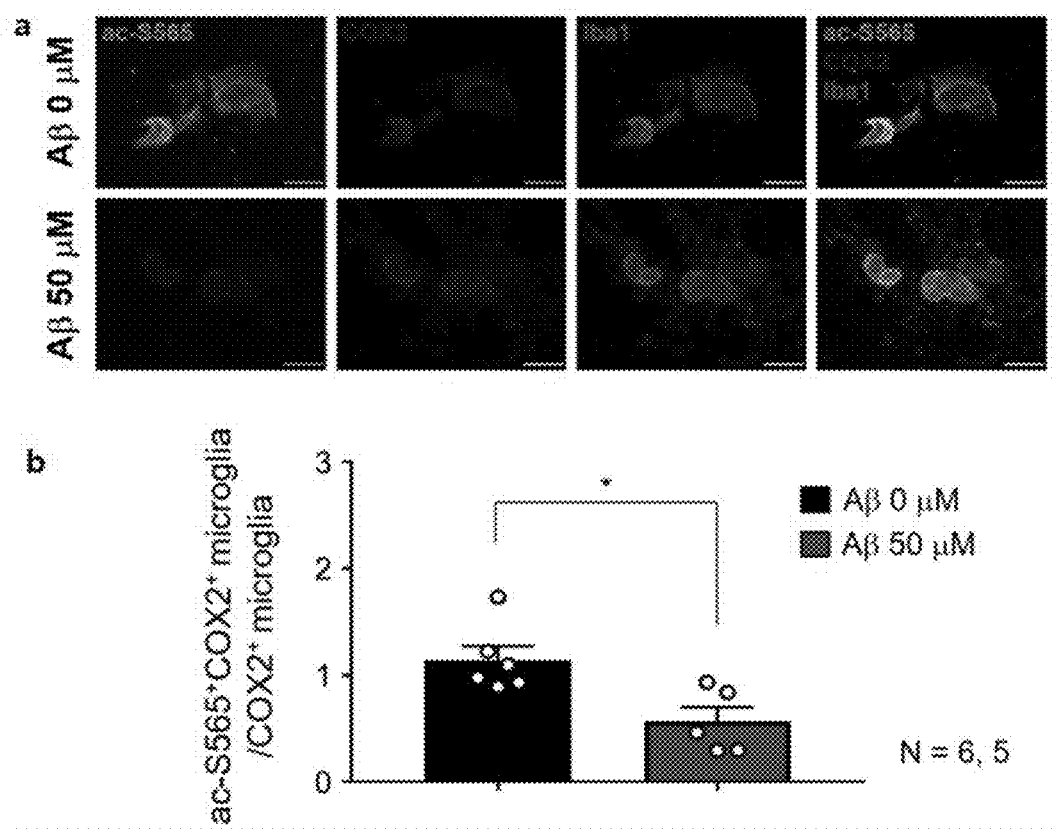
FIG. 13a illustrates a result of confirming the levels of acetylation of a COX2 protein and S565 of COX2 expressed in microglia derived from human treated with amyloid beta through fluorescence immunostaining.
FIG. 13b illustrates a result of quantifying the levels (n=4/group).

As a result, it was confirmed that when the amyloid beta was treated, the expression of COX2 was increased and the S565 acetylation of COX2 was decreased in the microglia. These results indicate that the level of S565 acetylation of COX2 is reduced in a neuroinflammatory environment due to the accumulation of amyloid beta (FIGS. 13a and 13b).

The present inventors created a neuroinflammatory environment by treating human-derived microglia with amyloid beta, and then reconfirmed the level of S565 acetylation of COX2 through Western blotting.

Figure 14:
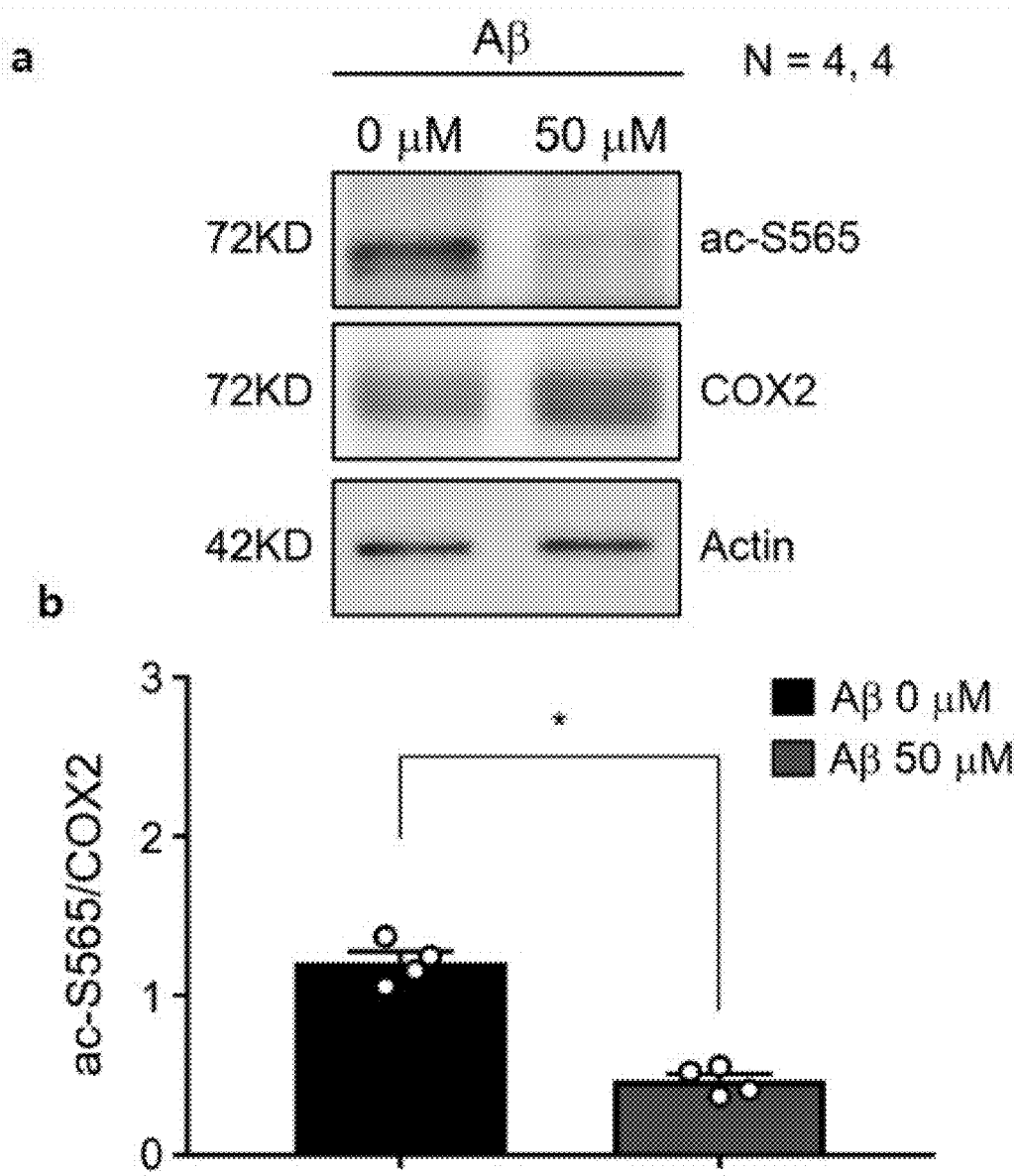
FIG. 14a illustrates a result of confirming the levels of acetylation of a COX2 protein and S565 of COX2 expressed in microglia derived from human treated with amyloid beta through Western blotting.
FIG. 14b illustrates a result of quantifying the levels (n=4/group).

As a result, like the fluorescence immunostaining result, it was confirmed that when the amyloid beta was treated, the expression of COX2 was increased and the S565 acetylation of COX2 was decreased in the microglia. These results indicate that the level of S565 acetylation of COX2 is reduced in a neuroinflammatory environment due to the accumulation of amyloid beta (FIGS. 14a and 14b).

Through this result, it can be confirmed that degenerative neurological diseases can be diagnosed by analyzing the level of S565 acetylation of COX2.

13. Confirmation of Reduction in COX2 S565 Acetylation Through Western Blot in Blood Cells (Monocytes) of Alzheimer's Animal Model In order to confirm the possibility of diagnosing degenerative neurological diseases by analyzing the level of COX2 S565 acetylation in blood cells (monocytes) of the blood as well as microglia, the present inventors confirmed the level of S565 acetylation of COX2 in blood cells (monocytes) of an Alzheimer's animal model (APP/PS1) through Western blot.

Figure 15:
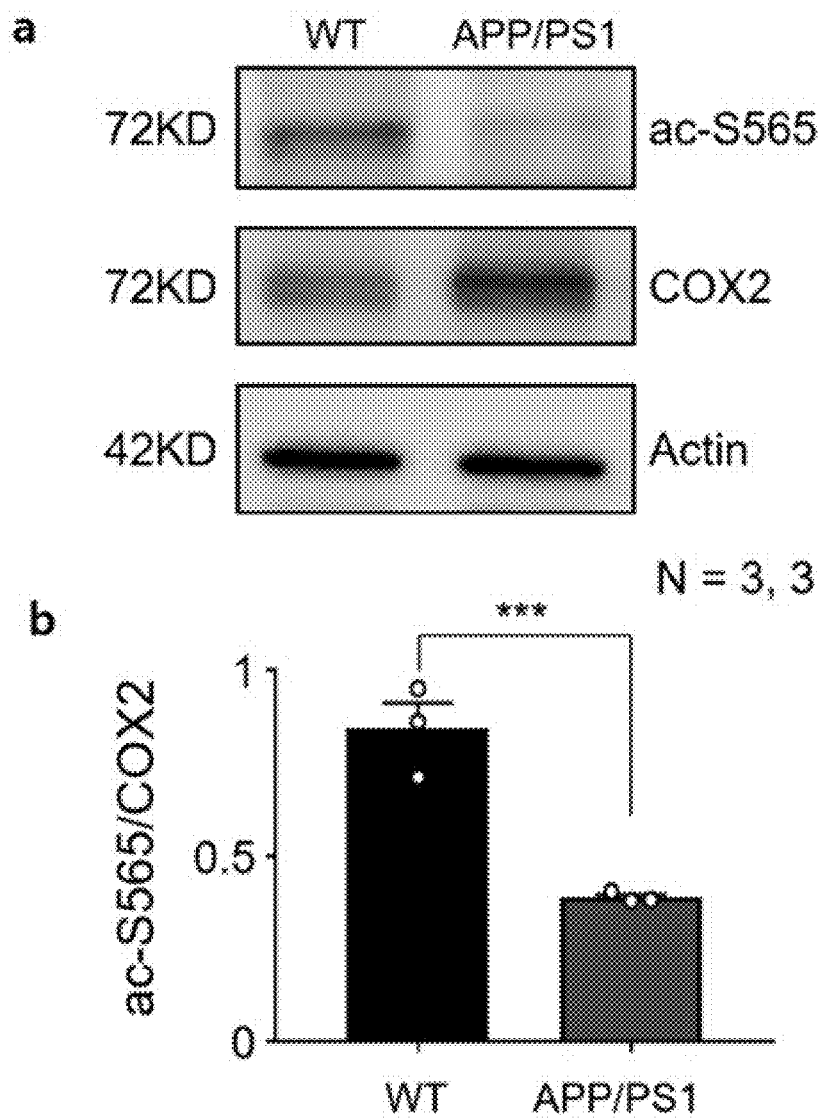
FIG. 15a illustrates a result of confirming the levels of acetylation of a COX2 protein and S565 of COX2 expressed in blood cells derived from wild-type and APP/PS1 mice through Western blotting.
FIG. 15b illustrates a result of quantifying the levels (n=3/group).

As a result, like the result, it was confirmed that the expression of COX2 was increased and the S565 acetylation of COX2 was decreased in the blood cells (monocytes) of the Alzheimer's animal compared to wild-type mice. These results indicate that the S565 acetylation of COX2 is reduced even in the blood cells (monocytes, monocytes) as well as the microglia of the Alzheimer's animal model, and it can be determined that degenerative neurological diseases can be easily diagnosed by analyzing the level of COX2 S565 acetylation in the blood cells (monocytes) of the blood (FIGS. 15a and 15b).

INDUSTRIAL APPLICABILITY

According to the present invention, since the acetylation of COX2 in degenerative neurological diseases is significantly reduced, whether COX2 is acetylated may be utilized as a diagnostic marker for degenerative neurological diseases, and it is possible to diagnose degenerative neurological diseases more rapidly and accurately by using same. Therefore, the present invention has industrial applicability.

What is claimed is:

1. A method of treatment, comprising:
   (a) providing a biological sample from a patient;
   (b) measuring the level of acetylation of COX2 (cyclooxygenase-2) in the sample;
   (c) identifying the sample as having a level of acetylation of the COX2 that is lower than that of a normal control sample; and
   (d) treating the patient for a degenerative neurological disease using a COX2 acetylating agent based on the results of step (c).

2. The method of claim 1, wherein the method for measuring the level of acetylation of COX2 is at least one selected from the group consisting of autoradiography, liquid scintillation counting, molecular weight assay, liquid chromatographic mass assay, Western blot, ELISA, radioimmunoassay, radioimmunodiffusion, Ouchterlony immunodiffusion, rocket immunoelectrophoresis, immunofluorescence staining, immunohistochemical staining, immunoprecipitation assay, complement fixation assay, FACS, and protein chip.

3. The method of claim 1, wherein the sample is selected from the group consisting of blood, blood cells, brain tissue, nerve cells, cerebrospinal fluid, saliva, nasal fluid, sputum, synovial fluid, amniotic fluid, ascites, cervical or vaginal secretions, and urine.

* * * * *